(12) United States Patent
O'Connor et al.

(10) Patent No.: US 6,864,054 B1
(45) Date of Patent: Mar. 8, 2005

(54) POLYPEPTIDES FROM CREB BINDING PROTEIN AND RELATED PROTEIN P300 FOR USE IN TRANSCRIPTIONAL REGULATION

(75) Inventors: Mark J. O'Connor, Cambridge (GB); Holger Zimmermann, Wuppertal (DE)

(73) Assignee: Institute of Molecular and Cell Biology, Singapore (SG)

( * ) Notice: Subject to any disclaimer, the term of this patent is extended or adjusted under 35 U.S.C. 154(b) by 0 days.

(21) Appl. No.: 09/701,080

(22) PCT Filed: May 26, 1999

(86) PCT No.: PCT/GB99/01668

§ 371 (c)(1),
(2), (4) Date: Feb. 27, 2001

(87) PCT Pub. No.: WO99/61608

PCT Pub. Date: Dec. 2, 1999

(30) Foreign Application Priority Data

May 26, 1998 (GB) ............................................... 9811303
Jan. 5, 1999 (GB) ............................................... 9900157

(51) Int. Cl.[7] .............................. C12Q 1/68; C12N 7/00
(52) U.S. Cl. ........................ 435/6; 435/235.1; 435/325; 435/91.1; 435/91.33; 435/69.1; 435/69.7; 530/300
(58) Field of Search .................... 435/6, 235.1, 325, 435/91.33, 91.1, 69.1, 69.7, 7.1; 530/300; 536/23.72

(56) References Cited

U.S. PATENT DOCUMENTS 5,821,051 A * 10/1998 Androphy et al. ............. 435/5

FOREIGN PATENT DOCUMENTS

| WO | WO 97/11367 | * 3/1997 |
| WO | WO 98/01467 | * 1/1998 |
| WO | 98/03652 | 1/1998 |

OTHER PUBLICATIONS

Zimmermann et al, Journal of Virology, Aug. 1999, vol. 73, No. 8, pp. 6209–6219.*

X Yang et al.: "A p300/CBP–association factor that competes with the adenoviral protein E1A" Nature., vol. 382, No. 8589, Jul. 1996, pp. 319–324, Macmillan Journals Ltd. London., GB.

D. Trouche et al.: "The CBP co–activator stimulates E2F1–DP1 activity" Nucleic Acids Research, vol. 24, No. 21, Nov. 1996, pp. 4139–4145, Oxford GB.

G Liang & T Hai: "Characterization of human activating transcription factor 4, a transcriptional activator that interacts with multiple domains of cAMP–responsive lement–binding (CREB)–binding protein (CBP)" Journal of Biological Chemistry., vol. 272, No. 38, Sep. 1997, pp. 14088–24095, American Society of Biological Chemists, Baltomore, MD., US.

Chemical Abstracts, vol. 127, No. 10, Sep. 1997, Columbus, Ohio, US; abstract No. 131884, V Facchinetti et al.: "Regulatory domains of the A–Myb transcription factor and its interaction with the CBP/p300 adaptor molecules" & Biochem. J., vol. 324, No. 3, 1997, pp. 729–736.

File Medline, abstract 97154536, 1997 & V Sartorelli et al.: "Molecular mechanisms of myogenic coactivation by p300; direct interaction with the activation domain of MyoD and with the MADS box of MEF2C" Molecular and Cellular Biology, vol. 17, No. 2, Feb. 1997, pp. 1010–1016.

M O'Connor et al.: "Characterization of an E1A–CBP interaction defines a novel transcriptional adapter motif (TRAM) in CBP–p300" Journal of Virology., vol. 73, No. 5, May 1999, pp. 3574–3581, The American Society for Microbiology., US.

* cited by examiner

*Primary Examiner*—Ali R. Salimi
(74) *Attorney, Agent, or Firm*—Nixon & Vanderhye P.C.

(57) ABSTRACT

A method for determining whether a compound inhibits or disrupts an interaction between a first polypeptide comprising a transcriptional adaptor motif (TRAM) and a second polypeptide comprising a TRAM-interaction motif. The first polypeptide and/or second polypeptide may be Mdm-2, p53, TBP, E2F, YY1, CBP/p300 or TF11B, or a viral polypeptide such as a human papillomavirus (HPV) E6 polypeptide from HPV strain (16) or (18).

9 Claims, 15 Drawing Sheets

Figure 1A:
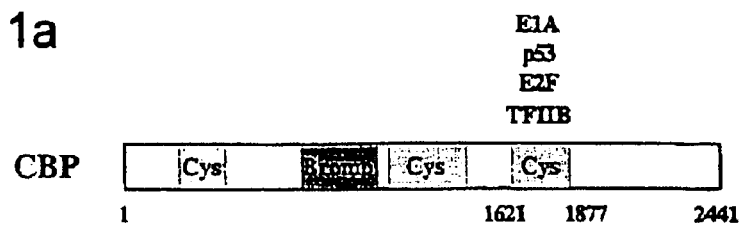

Figure 2b
| Peptides: | WT | : | V N E F F P E S L I L |
|---|---|---|---|
| | Mut 1 | : | V N E F F P A S A I L |
| | Mut 2 | : | V N E F A P A S A I A |
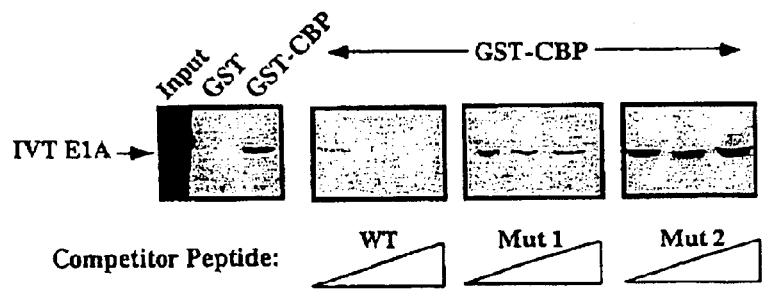
Figure 2c
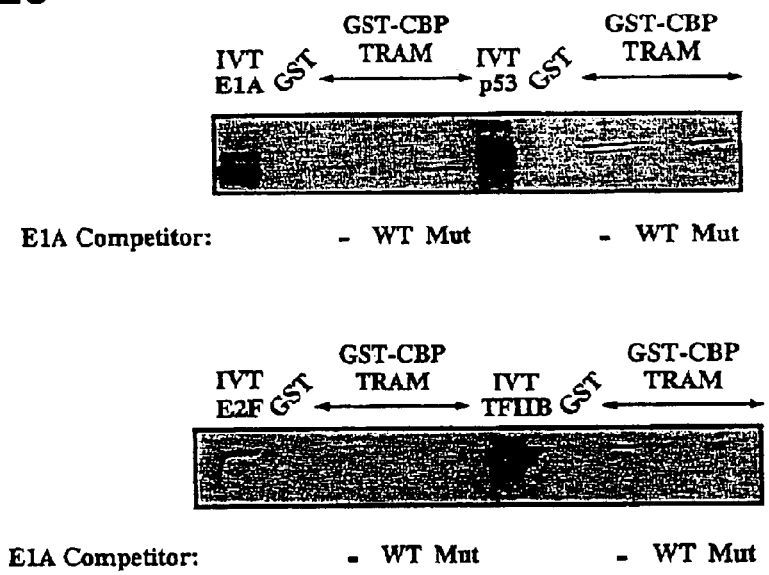
Figure 2d
| TRAM Interaction Motif | E1A | V N E F F P E S L I L A A |
|---|---|---|
| | p53 | S Q E T F S D L W K L L P |
| | E2F | F D C D F G D L T P L D F |
Consensus: $FX\frac{E}{D}XXXL$

Figure 6a
|  |  |  |
|---|---|---|
|  | E1A | VNEFFPESLILAA |
|  | p53 | SQETFSDLWKLLP |
|  | E2F | FDCDFGDLTPLDF |
| TRIMs | TFIIB | MMNAFKEITTMAD |
|  | YY1 | AEDGFEDQILIPV |
|  | YY1 | CTKMFRDNSAMRK |
|  | YY1 | CGKAFVESSKLKR |
|  | MyoD | TTDDFYDDPCFDS |
Figure 6b
|— CBP TRAM —|
1808 GCKRKTNGGCPVCKQLIAL 1826
Mutant:   1   2 3 4 5 6 7 8 9 10  11
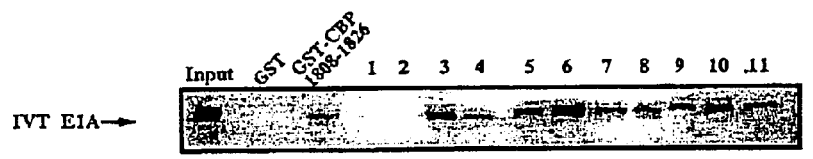
IVT E1A→
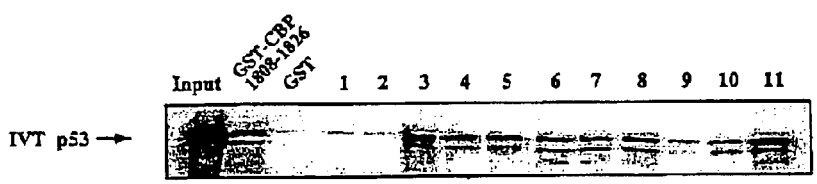
IVT p53→
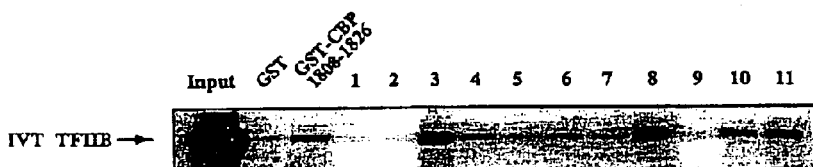
IVT TFIIB→
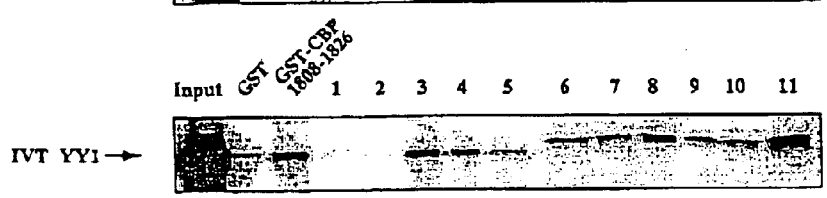
IVT YY1→

CBP (1808-1826): GCKRKTNGGCPVCKQLIAL
p300 (1770-1788): GCKRKTNGGCPICKQLIAL
               *********+*****

16 E6

```
     G   S   V   D   L   E   P   G   V   Q   K   L   x   x   x
    gGA TCC GTC GAC CTC GAG CCC GGG CTG CAG AAG CTT GAT TGA Tta gct t  3'
    cct agG CAG CTG GAG CTC GGG CCC GAC GTC TTC GAA CTA ACT AAT GGA a  5'
     BamH1   SalI    XhoI    SmaI    PstI    HindIII  stop (x3)  [core HindIII]
```

Figure 13

POLYPEPTIDES FROM CREB BINDING PROTEIN AND RELATED PROTEIN P300 FOR USE IN TRANSCRIPTIONAL REGULATION

FIELD OF THE INVENTION

The present invention relates to polypeptides which comprise TRanscriptional Adaptor Motif (TRAM) and/or TRAM-Interaction Motif (TRIM) sequences. These polypeptides may be used in assay methods to identify inhibitors of TRAM/TRIM interactions. They may also be used in methods of treating viral disease or cancer where a TRAM/TRIM interaction is important in disease initiation/progression.

BACKGROUND TO THE INVENTION

The control of the cell cycle, during which cells replicate their DNA and divide, is a cardinal step in normal human cell growth and in tissue differentiation, while de-regulation of this process can result in tumourigenesis and the onset of cancer. Protein-protein interactions play a crucial role in these events, with the regulation of gene expression in particular being central for the determination of cell cycle fate.

Recently, the transcriptional co-factor CBP (CREB binding protein) and the related protein p300 have been implicated in the control of cell cycle events. Interestingly, CBP has been shown to be required for both E2F activity which results in the expression of S phase specific genes and cellular proliferation, and for the expression of p21$^{WAF}$ by p53, which results in cell cycle arrest. Moreover, studies of cellular transformation by the adenovirus oncogene product E1A have shown that an interaction with CBP is necessary for this process. These observations suggest that two opposite cell cycle events rely upon an interaction with a common factor, CBP/p300.

CBP is a very large protein (2,441 amino acids) and can be thought of as a transcriptional adaptor with the capability of binding many different transcriptional factors. While a few regions of CBP have been described a "hot spots" for protein interactions, the mechanisms by which different proteins interact with CBP, and the exact motifs involved, have not been defined. Many of the proteins that regulate the cell cycle bind to the same 257 amino acid region of CBP (1621–1877). However, since a number of these proteins are thought to have antagonist effects, it would be useful to know if the same CBP sequences were recognized by these different proteins or if not, if the different motifs overlapped.

SUMMARY OF THE INVENTION

We have now identified a TRAM within CBP and also in the related p300. These TRAMs are conserved between species. They provide a consensus TRAM that has been shown to bind to multiple cellular regulators including the cellular transcription factors p53, E2F, TFIIB and YYI. However, TRAMs are not limited to CBP/p300 since one is also found in Mdm-2 proteins.

TRAM-interacting proteins may bind a TRAM sequence through different TRIMs. A TRIM therefore binds a TRAM sequence, typically a TRAM sequence of CBP or p300 or Mdm-2. One type of TRIM may be defined by the consensus sequence FXE/DXXXL. The variation seen in potential TRIMs led us to check a series of TRAM mutants (alanine-substitutions) against different TRAM-interacting proteins.

We found differential binding properties of TRAM variants with respect to TRAM-interacting proteins. Thus TRAM variants can be used to add specificity TRIM-TRAM interactions.

Since the TRIM/TRAM-containing proteins identified here are involved in the processes of transcriptional regulation, cell cycle control and viral infection, the identification of compounds which disrupt interactions between, for example cellular TRAM-containing proteins and cellular TRIM-containing proteins, or cellular TRIM/TRAM containing proteins and viral TRIM/TRAM proteins may allow these processes to be targeted in the treatment of, for example, tumours and viral diseases.

Accordingly the present invention provides a method for determining whether a compound is capable of inhibiting or disrupting an interaction between a first polypeptide and a second polypeptide said method comprising:
  (a) (i) incubating said first polypeptide with said second polypeptide under conditions which allow the first polypeptide to bind to the second polypeptide to form a complex; and bringing the complex thus formed into contact with a candidate compound; or
    (ii) incubating said first polypeptide with said second polypeptide in the presence of a candidate compound under conditions which would allow the first polypeptide to bind to the second polypeptide in the absence of the candidate compound; and
  (b) determining if said candidate compound inhibits or disrupts binding of the first polypeptide to the second polypeptide;
wherein said first polypeptide comprises a TRAM sequence and said second polypeptide comprises a TRIM sequence.

Preferably the candidate compound is a polypeptide comprising a TRAM and/or a TRIM sequence. Such a polypeptide preferably has at least 12 amino acids, more preferably at least 19, 30, 40 or 50 amino acids and preferably less than 200 amino acids, more preferably less than 100, 90, 80, 70 or 60 amino acids. The polypeptide may be shorter, for example up to 20 or up to 30 amino acids in length. Alternatively, the candidate compound may be a non-peptide organic or inorganic molecule.

The first polypeptide and/or said second polypeptide may a viral polypeptide, preferably a human papillomavirus (HPV) polypeptide, more preferably an HPV E6 polypeptide, most preferably an HPV E6 polypeptide from HPV strain 16 and 18. The first polypeptide and/or said second polypeptide may also be a polypeptide found in eukaryotic cells, for example a polypeptide selected from transcription factors and cell cycle regulatory proteins. Preferably, the first and/or second polypeptide is selected from Mdm-2, p53, TBP, E2F, YY1, CBP/p300 and TFIIB.

A TRIM or TRAM-containing polypeptide may itself be used to disrupt an interaction between a TRIM-containing polypeptide and a TRAM-containing polypeptide. For example, an oligopeptide consisting essentially of the TRIM sequence of E1A or p53 or an oligopeptide consisting essentially of the TRAM sequence of Mdm-2 may be introduced into a tumour cell over-expressing Mdm-2 to prevent Mdm-2-mediated inhibition of the p53-mediated cell cycle arrest/apoptotic pathway resulting in death of the tumour cell.

Accordingly, the present invention also provides the use of a compound in a method of disrupting an interaction between a first polypeptide and a second polypeptide, wherein said compound is a polypeptide comprising a TRAM sequence and/or a TRIM sequence, said first polypeptide comprises a TRAM sequence and/or said second polypeptide comprises a TRIM sequence.

The present invention further provides the use of a compound in an in vitro method of disrupting an interaction between a first polypeptide and a second polypeptide, wherein said compound is a polypeptide comprising a TRAM sequence and/or a TRIM sequence, said first polypeptide comprises a TRAM sequence and/or said second polypeptide comprises a TRIM sequence.

As discussed above, the disruption of TRIM-TRAM interactions will have clinically important applications. Thus, the present invention also provides the use of a compound in the manufacture of a medicament for use in a method of disrupting an interaction between a first polypeptide and a second polypeptide, wherein said compound is a polypeptide comprising a TRAM sequence and/or a TRIM sequence, said first polypeptide comprises a TRAM sequence and/or said second polypeptide comprises a TRIM sequence.

Preferably the uses described above are where the disruption of said interaction inhibits virai transcription, or inhibits cell cycle progression in mammalian cells, preferably a cancer cell.

The present invention further provides a pharmaceutical composition comprising a polypeptide comprising a TRAM and/or TRIM sequence.

The present invention also provides a polypeptide in substantially isolated form consisting essentially of a TRAM and/or TRIM sequence.

The present invention further provides a polynucleotide molecule comprising a coding region encoding a polypeptide of the invention, preferably a polypeptide consisting essentially of a TRAM and/or TRIM sequence. The polynucleotide may also comprise additional coding region linked to, and in frame with, the coding region encoding a polypeptide of the invention. Polynucleotides of the invention may also be incorporated into nucleic acid vectors to produce a nucleic acid vector of the present invention.

TRAM/TRIM-containing polypeptides of the invention may also be used to identify novel TRAM/TRIM-containing polypeptides, for example polypeptides involved in cell cycle control and/or transcriptional regulation.

Accordingly the present invention provides a method for identifying a compound which interacts with a polypeptide comprising a TRAM sequence and/or a TRIM sequence which method comprises:

(a) incubating a candidate compound with a polypeptide comprising a TRAM sequence and/or a TRIM sequence under suitable conditions; and (b) determining if said candidate compound interacts with said polypeptide comprising a TRAM sequence and/or a TRIM sequence;

DETAILED DESCRIPTION OF THE INVENTION

Unless indicated otherwise, the techniques and methodologies described are standard biochemical techniques. Examples of suitable general methodology textbooks include Sambrook et al., Molecular Cloning, A Laboratory Manual (1989) and Ausubel et al., Current Protocols in Molecular Biology (1995), John Wiley & Sons, Inc.

A. Polypeptides

Polypeptides of the invention consist essentially of a TRanscriptional Adaptor Motif (TRAM) and/or a TRAM Interaction Motif (TRIM). Preferably polypeptides of the invention are truncated variants of full-length TRAM- and/ or TRIM-containing polypeptides, but may be such a full-length polypeptide. Thus, for example, polypepuides of the invention may consist essentially of at least 12 amino acids, preferably at least 19 amino acids, more preferably at least 30, 40 or 50 amino acids, but preferably less than 200 amino acids, more preferably less than 150 amino acids, most preferably less than 100, 90, 80, 70 or 60 amino acids. The polypeptide may be shorter, for example up to 20 or up to 30 amino acids in length.

Polypeptides of the invention may, however, be part of a larger polypeptide, for example a fusion protein. In this case, the additional polypeptide sequences are preferably polypeptide sequences with which the polypeptide of the invention is not normally associated.

A TRAM sequence of the invention is a minimal amino acid sequence which can interact with a protein capable of binding to a wild-type TRAM sequence. Such wild-type sequences are the wild-type CBP, Mdm-2 and p300 TRAM sequences noted below. Variants of a wild-type sequence may thus be used to provide specific instructions with a subset of the proteins that normally bind the wild-type TRAM.

A suitable TRAM sequence is one which binds the consensus TRIM sequence FX[E/D]XXXL (leucine can be replaced with a similar neutral non-polar residue such as isoleucine, valine, methionine or phenylalanine). Preferably, a TRAM sequence consists essentially of the following:

(i) two or more basic residues at, or near such as within four, three or two amino acid residues of, the N-terminus;

(ii) a cysteine-proline-valine/isoleucine-cysteine (CP[V/I]C) sequence, which is preferably part of a zinc finger motif;

(iii) an asparagine (N) residue between (i) and (ii); and (iv) a basic residue immediately following the CP[V/I]C sequence.

More preferably, the TRAM sequence also contains an isoleucine residue at, or near such as within four, three or two amino acid residues of, the C-terminus. Particularly preferred examples of TRAM sequences of the invention are polypeptides consisting essentially of:

[K/R, K/R] XNXXCP [V/I] C [K/R] X (SEQ ID NO. 1)

[K/R, K/R] XNXXCP [V/I] C [K/R] XI (SEQ ID NO. 2)

RKTNGGCPVCKQ (SEQ ID NO. 3—derived from CBP)

RKTNGGCPVCKQPI (SEQ ID NO. 4—derived from CBP)

GCKRKTNGGCPVCKQLIAL (SEQ ID NO. 5—derived from CBP)

KKRNKPCPVCRQ (SEQ ID NO. 6—derived from Mdm-2)

KKRNKPCPVCRQPI (SEQ ID NO. 7—derived from Mdm-2)

RKTNGGCPICKQ (SEQ ID NO. 8—derived from p300)

RKTNGGCPICKQLI (SEQ ID NO. 9—derived from p300)

SEQ ID NOS: 3 to 9 are wild-type TRAM sequences. Examples of TRIM-containing polypeptides which may be used to determine whether a candidate TRAM sequence functions as such include E1A, E2F, p53, TFIIB, YY1 and MyoD and certain HPV E6 variants. Full-length CBP, Mdm-2 or p300 may be used as the first, TRAM-containing, polypeptide in the present invention.

A TRIM sequence of the invention is a minimal amino acid sequence which can bind the consensus TRAM sequence [K/R, K/R] XNXXCP [V/I] C [K/R] X. A TRIM sequence may thus bind the consensus TRAM sequence [K/R,K/R]XNXXCP[V/I]C[K/R]XI or one or more of the wild-type TRAM sequences. A TRIM sequence is thus capable of binding a polypeptide containing such a TRAM sequence.

A suitable TRIM sequence consists essentially of the consensus sequence FX[E/D]XXXL (leucine can be replaced with a similar neutral non-polar residue such as isoleucine, valine, methionine or phenylalanine). Particularly preferred examples of TRIM sequences of the invention are polypeptides consisting essentially of:

FX[E/D]XXXL (SEQ ID NO. 10)
FPESLIL (SEQ ID NO. 11—derived from E1A)
FSDLWKL (SEQ ID NO. 12—derived from p53)
FKEITTM (SEQ ID NO. 13—derived from TFIIB)
FEDQILI (SEQ ID NO. 14—derived from YY1)
FRDNSAM (SEQ ID NO. 15—derived from YY 1)
FVESSKL (SEQ ID NO. 16—derived from YY 1)
FYDDPCF (SEQ ID NO. 17—derived from MyoD)

A TRIM sequence is also located with the second zinc finger of HPV-16 or -18 E6 protein, in particular between HPV-16 E6 residues 100 to 147 and between the corresponding residues of HPV-18 E6 protein. Examples of TRAM-containing polypeptides which may be used to determine whether a candidate TRIM sequence functions as such include CBP, p300 and Mdm-2. Full length E1A, p53, TFIIB, YYI, MyoD, HPV-16 E6 or HPV-18 E6 may be used as the second TRIM-containing, polypeptide in the invention.

Polypeptides comprising TRIM/TRAM sequences may be modified to provide polypeptides of the invention. Amino acid substitutions may be made, for example from 1, 2 or 3 to 10, 20 or 30 substitutions provided that the modified polypeptide retains substantially similar TRIM/TRAM binding activity (for example at least 70, 80 or 90% of the binding activity of the non-modified polypeptide). Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Alternatively, mutations may be made which reduce or abolish the binding ability of TRIM/TRAM sequences to produce derivatives which may be used, for example, to study the role of a TRIM/TRAM-containing polypeptide in cell cycle control and/or viral infection.

In addition, polypeptides of the invention may be cyclized, for example as described in U.S. Pat. No. 5,723, 575. Cyclization of polypeptides, in particular small peptides, can be used to confer conformational constraints on such peptides, which may be advantageous in drug design.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99%, by weight of the polypeptide in the preparation is a polypeptide of the invention.

Polypeptides of the invention may be made by synthetic means or recombinantly using techniques well known to skilled persons. Polypeptides of the invention may also be produced as fusion proteins. Examples of fusion protein partners include glutathione-S-transferase (GST), 6×His, GAL4 (DNA binding and/or transcriptional activation domains) and β-galactosidase.

Polypeptides of the invention may be used in in vitro or in vivo cell culture systems to study the role of TRIM/TRAM interactions in cellular control mechanisms, particularly with respect to the ways in which viral TRIM/TRAM containing polypeptides circumvent such control mechanisms, for example the E6 protein of HPV. For example, TRIM/TRAM polypeptides may be introduced into a cell to disrupt the normal functions that occur in the cell. They may also be introduced into a cell before, concomitant with, or after viral infection to determine if virus growth and propagation can be inhibited. The polypeptides of the invention may be introduced into the cell by in situ expression of the polypeptide from a recombinant expression vector (see below). The expression vector optionally carries an inducible promoter to control the expression of the polypeptide.

The use of mammalian host cells is expected to provide for such post-translational modifications (e.g. myristolation, glycosylation, truncation, lapidation and tyrosine, serine or threonine phosphorylation) as may be needed to confer optimal biological activity on recombinant expression products of the invention. Such cell culture systems in which polypeptides of the invention are expressed may be used in assay systems to identify candidate substances which interfere with or enhance the functions of TRIM/TRAM containing polypeptides in the cell.

Polypeptides of the invention may also be used to produce antibodies against the TRIM or TRAM sequences. Antibodies may be polyclonal or monoclonal. Techniques for producing antibodies are well known to persons skilled in the art (see for example, Harlow and Lane, 1988. Antibodies: .A Laboratory Manual. CSH Laboratory. Cold Spring Harbor, N.Y.)

B. Polynucleotides and Vectors

Polynucleotides of the invention comprise nucleic acid sequences encoding the polypeptides of the invention. Polynucleotides of the invention may comprise DNA or RNA. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Preferred polynucleotides of the invention include polynucleotides encoding any of the polypeptides of the invention described above. It will be understood by a skilled person that numerous different polynucleotides can encode the same polypeptide as a result of the degeneracy of the genetic code.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide of the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Such vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptides, and optionally recovering the expressed polypeptides.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in a method of gene therapy.

Promoters/enhancers and other expression regulation signals may be selected to be compatible with the host cell for which the expression vector is designed. For example, mammalian promoters, such as β-actin promoters, may be used. Tissues-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, herpes simplex virus promoters or adenovirus promoters. All these promoters are readily available in the art.

C. Viral Vectors

The polynucleotides of the invention may be used in the form of a naked nucleic acid construct. Alternatively, they may be introduced into a variety of nucleic acid vectors. Such vectors include plasmids and viral vectors, preferably herpes simplex virus vectors. Vectors may further include sequences flanking a polynucleotide of the invention which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the polynucleotide of the invention flanked by viral sequences, can be used to prepare a viral vector, suitable for delivering the polynucleotides of the invention to a mammalian cell. The techniques employed are well-known to a skilled person. Examples of suitable viral vectors include herpes simplex virus vectors and viral vectors able to integrate their genomes into the host cell genome, for example retroviruses, including lentiviruses, and adeno-associated virus.

D. Candidate Substances for Use in Assay Methods

Interactions between TRAM-containing polypeptides (for example Mdm-2 or CBP) and TRIM-containing polypeptides (for example p53) are important in cell cycle regulation, transcriptional regulation and viral infection. The identification, reported here, of the minimal consensus motifs through which these interactions are mediated, has important implications in several areas, for example drug design. In particular, nearly all protein-protein interaction surfaces identified to date have been quite large. This has made it difficult to identify small organic or inorganic molecules that can disrupt such interactions. The TRIM and TRAM motifs identified here represent some of the smallest interaction interfaces described to date. Thus a screening approach using peptides containing these motifs is likely to be more successful in identifying low molecular weight compounds capable of disrupting the protein-protein interactions than screens based on more extensive interaction surfaces. Identification of substances which disrupt an interaction between the a TRAM-containing polypeptide and a TRIM-containing polypeptide may result in the development of drugs which can modulate transcription, cell cycle control and viral infection in a therapeutically useful way. In addition, the knowledge that these TRAM and TRIM motifs are important in these interactions will allow identification of other components of cellular and viral machinery that are involved in the processes of transcription, cell cycle control and viral infection.

A substance which disrupts an interaction between a TRAM-containing polypeptide (a first polypeptide) and a TRIM-containing polypeptide (a second polypeptide) may do so in several ways. It may directly disrupt the binding of the two components by, for example, binding to one component and masking or altering the site of interaction with the other component. Candidate substances of this type may conveniently be screened by in vitro binding assays as, for example, described below. Examples of candidate substances include polypeptides containing TRIM and/or TRAM sequences, other organic and inorganic low molecular weight compounds as well as antibodies which recognize the first or second polypeptides.

Candidate TRIM and/or TRAM containing polypeptides may conveniently be identified using database searches to locate polypeptide sequences which match the TRIM and/or TRAM consensus sequences given in, for example SEQ ID. NO. 1 or 9, or which have homology to the TRIM and/or TRAM sequences identified in actual polypeptides, for example Mdm2, CBP, E6 and p53.

A substance which can bind directly to the first or second component may also inhibit an interaction between the first polypeptide and the second polypeptide by altering their subcellular localisation thus preventing the two components from coming into contact within the cell. This can be tested in vivo using, for example the in vivo assays described below. The term 'in vivo' is intended to encompass experiments with cells in culture as well as experiments with intact multicellular organisms.

Alternatively, instead of preventing the association of the components directly, the substance may suppress or enhance the biologically available amount of one or both of the components. This may be by inhibiting expression of the component, for example at the level of transcription, transcript stability, translation or post-translational stability. An example of such a substance would be antisense RNA which suppresses the amount of first or second polypeptide mRNA translated into protein.

Suitable candidate substances include peptides comprising TRIM and/or TRAM sequences, especially of from about 12 to 20 amino acids in size. Peptides from panels of peptides comprising random sequences or sequences which have been varied consistently to provide a maximally diverse panel of peptides may be used. Cyclized versions of these peptides may also be used.

Suitable candidate substances also include antibody products (for example, monoclonal and polyclonal antibodies, single chain antibodies, chimeric antibodies and CDR-grafted antibodies) which are specific for the first component or the second component. Furthermore, combinatorial libraries, peptide and peptide mimetics, defined chemical entities, oligonucleotides, and natural product libraries may be screened for activity as inhibitors of an interaction between the first polypeptide and the second polypeptide in assays such as those described below. The candidate substances may be used in an initial screen in batches of, for example 10 substances per reaction, and the substances of those batches which show inhibition tested individually. Candidate substances which show activity in in vitro screens such as those described below can then be tested in in vivo systems, such as mammalian cells which will be exposed to the inhibitor and tested for susceptibility to viral infection or apoptosis as appropriate.

An important observation, detailed in Example 1, is that TRAM variants can show differential binding to different TRIM sequences. Therefore, it will be desirable to test variants of TRAM sequences or TRIM sequences to determine specificity. This will be especially important for therapeutic applications where specificity is likely to be a critical consideration.

E. Assays

The assay methods of the invention may be in vitro assays or in vivo assays, for example using an animal model. One type of in vitro assay for identifying substances which disrupt an interaction between the first polypeptide (containing a TRAM sequence) and the second polypeptide (containing a TRIM sequence) involves:

- contacting a first polypeptide, which is immobilised on a solid support, with a non-immobilised second polypeptide in the absence of a candidate substance;
- contacting the first immobilised polypeptide with the non-immobilised second polypeptide in the presence of a candidate substance; and
- determining if the candidate substance disrupts the interaction between the first polypeptide and the second polypeptide.

Alternatively, the second polypeptide may be immobilised and first polypeptide non-immobilised.

In a preferred assay method, the first polypeptide is immobilised on beads such as agarose beads. Typically this is achieved by expressing the component as a GST-fusion protein in bacteria, yeast or higher eukaryotic cell lines and purifying the GST-fusion protein from crude cell extracts using glutathione-agarose beads (Smith and Johnson, 1988). As a control, binding of the second polypeptide, which is not a GST-fusion protein, to the immobilised first polypeptide is determined in the absence of the candidate substance. The binding of the second component to the immobilised first polypeptide is then determined in the presence of the candidate substance. Any inhibitory effect by the candidate substance can then be evaluated. This type of assay is known in the art as a GST pulldown assay (see methods).

The candidate substance may be pre-incubated with the first polypeptide or with the second polypeptide or added to the reaction mixture after pre-incubation of the first polypeptide with the second polypeptide. In a similar assay, the second polypeptide is a GST fusion protein immobilised on glutathione agarose beads and the first polypeptide is not a GST-fusion protein. It is also possible to perform this type of assay using different affinity purification systems for immobilising one of the polypeptides, for example Ni-NTA agarose and histidine-tagged polypeptides, MBP-tagged polypeptides. Alternatively, polypeptides may be immobilised by covalent linkage via, for example, activated cyanogen bromide.

Binding of the first polypeptide to the second polypeptide (and vice-versa) may be determined by a variety of methods well-known in the art. For example, the non-immobilised polypeptide may be labelled (with for example, a radioactive label, an epitope tag or an enzyme-antibody conjugate). The effect of a candidate substance on an interaction between the two polypeptides can be determined by comparing the amount of label bound in the presence of the candidate substance with the amount of label bound in the absence of candidate substance. A lower amount of label bound in the presence of the candidate substance indicates that the candidate substance is an inhibitor of interactions between the first polypeptide and the second polypeptide. For example, typically for a candidate substance to be selected as an inhibitor of the interaction between the first and the second polypeptide, the amount of second polypeptide which binds to the first polypeptide (as indicated, for example, by the amount of bound label) in the presence of the inhibitor is at least 50%, preferably at least 75%, more preferably at least 80, 90, 95%, of the amount of second polypeptide which binds to the first polypeptide in the absence of the inhibitor. Similar considerations will apply to the various assays systems used, for example where binding is determined by transcriptional activation (as described below) or in a functional in vivo assay such as an assay which measures the degree of p53-mediated apoptosis or cell cycle arrest.

Alternatively, binding may be determined by immunological detection techniques. For example, the reaction mixture can be Western blotted and the blot probed with an antibody that detects the non-immobilised polypeptide. ELISA techniques may also be used.

Another method contemplated by the invention for identifying a substance that disrupts an interaction between the first polypeptide and the second polypeptide involves immobilising the first polypeptide on a solid support coated (or impregnated with) a fluorescent agent, labelling the second polypeptide with a substance capable of exciting the fluorescent agent, contacting the immobilised first polypeptide with the labelled second polypeptide in the presence and absence of a test compound, detecting light emission by the fluorescent agent, and identifying inhibitory substances as those candidate substances that reduce the emission of light by the fluorescent agent in comparison to the emission of light by the fluorescent agent in the absence of the test compound. Alternatively, the second polypeptide may be immobilised and the first polypeptide labelled in the assay.

Assays for identifying compounds that disrupt an interaction between the first and second polypeptide may also involve:

(a) transforming or transfecting an appropriate host cell with a DNA construct comprising a reporter gene under the control of a promoter regulated by a transcription factor having a DNA-binding domain and an activating domain;

(b) expressing in the host cell a first hybrid DNA sequence encoding a first fusion of the first polypeptide and the DNA binding domain or the activating domain of the transcription factor; expressing in the host cells a second hybrid DNA sequence encoding the second polypeptide and the DNA binding domain or activating domain of the transcription factor which is not incorporated in the first fusion;

(c) evaluating the effect of a test compound on the interaction between the first polypeptide and the second polypeptide by detecting binding of the first polypeptide to the second polypeptide in a particular host cell by measuring the production of reporter gene product in the host cell in the presence or absence of the test compound; and (d) determining whether the presence of the test compound alters the production of the reporter gene product in comparison to the production of the reporter gene product in the absence of the test compound.

The host cell may be a bacterium or other microbial cell. It may be a yeast or mammalian cell. Presently preferred for use in such an assay are a lexA promoter to drive expression of the reporter gene, the lacZ reporter gene, a transcription factor comprising the lexA DNA domain and the GAL4 transactivation domain and yeast host cells.

The candidate substance, i.e. the test compound, may be administered to the cell in several ways. For example, it may be added directly to the cell culture medium or injected into the cell. Alternatively, in the case of polypeptide candidate substances, the cell may be transfected with a nucleic acid construct which directs expression of the polypeptide in the cell. Preferably, the expression of the polypeptide is under the control of a regulatable promoter.

TRIM and/or TRAM containing polypeptides and candidate substances that are identified by the method of the invention as disrupting an interaction between a first polypeptide and a second polypeptide may be tested for their ability to, for example, reduce susceptibility of cells to viral infection or regulate the cell cycle including apoptosis and growth arrest. Such compounds could be used therapeutically to prevent or treat viral infection. They may also be used therapeutically in regulating the cell cycle of a mammalian cell, including inducing cell death in, for example, tumour cells.

Typically, an assay to determine the effect of a candidate substance (which may be a TRIM and/or TRAM-containing polypeptide or a substance identified by the method of the invention) on the susceptibility of cells to viral infection comprises:

(a) administering a virus, for example HPV, to a cell, for example primary human keratinocytes, in the absence of the candidate substance;

(b) administering the virus to the cell in the presence of the candidate substance; and (c) determining if the candidate substance reduces or abolishes the susceptibility of the cell to viral infection.

The candidate substance may be administered before, or concomitant with, the virus to establish if infection is prevented. Alternatively, the candidate substance may be administered subsequent to viral infection to establish if viral infection can be treated using the candidate substance. Administration of candidate substances to cells may be performed as described above.

The assay is typically carried out in vitro but an animal model could be employed instead. The virus is contacted with cells, typically cells in culture. The cells may be cells of a mammalian cell line, in particular mammalian cells susceptible to infection by the virus in the absence of the candidate substance.

Techniques for assaying infectivity of viruses are well-known in the art. As well as using plaque assays, levels of viral infection can be determined by using recombinant viruses which comprise a reporter gene, for example lacZ. The use of a histochemically detectable reporter gene is especially preferred when experiments are performed with animals, for example mice.

Typically, an assay to determine the effect of a TRIM and/or TRAM-containing polypeptide or candidate substance identified by the method of the invention on the regulation of the cell cycle in a mammalian cell comprises:

(a) administering the candidate substance to the cell; and (b) determining the effect of the candidate substance on the cell cycle, including, for example induction of cell cycle arrest and/or cell death by apoptosis.

Administration of candidate substances to cells may be performed as described above. The assay is typically carried out in vitro. The candidate substance is contacted with the cells, typically cells in culture. The cells may be cells of a mammalian cell line.

The ability of a candidate substance to induce apoptosis can be determined by administering a candidate compound to cells and determining if apoptosis is induced in said cells. The induction of apoptosis can be determined by various means. There are several techniques known to a skilled person for determining if cell death is due to apoptosis. Apoptotic cell death is characterized by morphological changes which can be observed by microscopy, for example cytoplasmic blebbing, cell shrinkage, internucleosomal fragmentation and chromatin condensation. DNA cleavage typical of the apoptotic process can be demonstrated using TUNEL and DNA ladder assays.

Several techniques known in the art for inducing apoptosis in cells may be used. For example, apoptosis may be induced by stress including UV or gamma irradiation exposure, growth factor deprivation and heat shock. The ability of the candidate substance to inhibit such apoptosis may be determined by comparing cells exposed to stress in the presence of the candidate substance with those exposed to stress in the absence of the candidate substance.

In a preferred embodiment of the above-described assays, TRIM and/or TRAM containing polypeptides, or derivatives thereof are used in an experimental system to study normal cellular interactions. For example, polypeptides containing derivatives of TRIM and/or TRAM sequences, including deletion, insertion and substitution mutants, can be used to disrupt an interaction between a TRIM-containing polypeptide and/or a TRAM-containing polypeptide. This can be tested in vitro using the in vitro assays described above. These interaction can also be disrupted in vivo by introducing TRIM and/or TRAM containing polypeptides and derivatives thereof, including deletion, insertion and substitution mutants, into cells in vivo, preferably mammalian cells, more preferably human cells. TRIM and/or TRAM containing polypeptides and their derivatives can be introduced into the cells using techniques described above. The effect of this disruption can be determined using immunoprecipitation studies or, alternatively, by analyzing the effect on cell cycle control using, for example, the assays and techniques described above. Any in vitro data obtained may be used to assist in the rational design of TRIM and/or TRAM containing polypeptides or derivatives thereof for use in the in vivo studies.

In addition to identifying substances which disrupt an interaction between a TRAM-containing polypeptide and a TRIM-containing polypeptide, the polypeptides of the invention may be used in an assay/screening method to identify substances which bind to a TRAM sequence or a TRIM sequence. This may result in the identification of novel components of cellular or viral machinery involved in cell cycle control, transcription and/or viral infection. Thus the present invention provides a method for identifying a compound which interacts with a polypeptide comprising a TRAM sequence and/or a TRIM sequence which method comprises:

(a) incubating a candidate compound with a polypeptide comprising a TRAM sequence and/or a TRIM sequence under suitable conditions; and (b) determining if said candidate compound interacts with said polypeptide comprising a TRAM sequence and/or a TRIM sequence.

Typically, such assays are carried out in vitro using similar formats to those described above (for example incubating a candidate substance with a TRIM/TRAM polypeptide immobilised on a solid phase (for example a GST pulldown assay) and interactions determined by similar techniques to, those described above. These assays may thus be used to screen, for example, crude or partially-purified cellular extracts for novel TRIM/TRAM polypeptides which may be part of the cellular signal transduction, cell cycle control, transcriptional control machinery, or involved in viral infection. It may also be used to identify candidate substances for use in the assays described above.

F. Diagnostic Uses

It has been shown in the Examples that different types of human papillomavirus have E6 polypeptides with different TRAM-binding properties. For example, the E6 polypeptides of two types which are known to be associated with a high risk of cervical cancer (HPV-16 and HPV-18) can bind the CBP TRAM sequence. They contain a consensus TRIM sequence. The E6 polypeptides of two types which are known to be associated with a low risk of cervical cancer (HPV-6 and HPV-11) do not bind CBP TRAM sequence. They do not contain a consensus TRIM sequence. Consequently, assays may be used to distinguish HPV types associated with a high risk of cervical cancer from HPV types associated with a low risk of cervical cancer on the basis of selective binding to a TRAM sequence, in particular the CBP TRAM sequence. Such assays may take the form of immunoassays or polypeptide/polypeptide binding assays.

G. Therapeutic Uses

All of the specific TRIM/TRAM polypeptides described above are part of polypeptides known to be involved in transcriptional regulation of genes involved in signal transduction and/or cell cycle control (for example, p53, Mdm-2, CBP/p300 and HPV E6). Consequently, a substance which disrupts an interaction between these TRIM/TRAM containing polypeptides (which may, for example, be identified by the assay methods of the invention is likely to have an effect on transcriptional regulation and/or cell cycle control. Thus such a substance may be used to regulate transcription and/or the cell cycle of a mammalian cell. Accordingly, the present invention provides a substance capable of disrupting an interaction between (i) a TRAM-containing polypeptide and (ii) a TRIM-containing polypeptide for use in a method of regulating the mammalian cell cycle. It also provides such a substance for use in a method of regulating cellular transcription. Typically, said substance may be used to induce cell death, for example in a tumour cell, or to prevent cell death. Examples of such substances include TRIM and/or TRAM containing polypeptides. As an example, a TRIM-containing polypeptide or a TRAM-containing polypeptide introduced into a tumour cell which is over-expressing Mdm-2 may be used to inhibit the interaction between Mdm-2 and p53 and allow p53-mediated apoptosis to proceed.

If either or both of the TRIM/TRAM polypeptides are of viral origin, then it may be possible to inhibit or reduce interactions that are required for viral infection, growth and/or propagation. For example, a TRAM-containing polypeptide may be used to inhibit the binding of HPV E6 to CBP. Accordingly, the present invention provides a substance capable of disrupting an interaction between (i) a TRAM-containing polypeptide and (ii) a TRIM-containing polypeptide for use in a method of preventing or treating viral infection, in particular HPV infection. In the case of a TRAM-containing polypeptide used to inhibit the binding of HPV E6 to CBP, it is preferred to use a TRAM sequence which is specific for the TRIM sequence of E6 from HPV-16 or HPV-18 (or another HPV type known to be associated with cervical cancer). This is because, as discussed above, it has been shown in the Examples that the E6 polypeptides of HPV types which are known to be associated with a high risk of cervical cancer (HPV-16 and HPV-18) can bind a CBP TRAM sequence whereas the E6 polypeptides of two HPV types which are known to be associated with a low risk of cervical cancer (HPV-6 and HPV-11) do not bind the CBP TRAM sequence.

The formulation of a substance according to the invention will depend upon the nature of the substance, for example whether it is a polypeptide or a non-peptide organic or inorganic molecule, but typically a substance may be formulated for clinical use with a pharmaceutically acceptable carrier or diluent. For example it may formulated for topical, parenteral, intravenous, intramuscular, subcutaneous, intraocular or transdermal administration. A physician will be able to determine the required route of administration for any particular patient and condition.

The polynucleotides of the invention may be administered directly as a naked nucleic acid construct, preferably further comprising flanking sequences homologous to the host cell genome. Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

Preferably, the substance is used in an injectable form. It may therefore be mixed with any vehicle which is pharmaceutically acceptable for an injectable formulation, preferably for a direct injection at the site to be treated. The pharmaceutically carrier or diluent may be, for example, sterile or isotonic solutions. It is also preferred to formulate that substance in an orally active form. Typically, said substance may be a polypeptide, an antibody or a nucleic acid construct. Nucleic acid constructs may be administered by various well-known techniques including lipofection, biolistic transformation or the use of viral vectors. Virus-like particles (VLPs) may also be used to deliver polynucleotides of the invention. VLPs can be generated by techniques known in the art. For example, VLPs formed in cell culture from the over-expression of the L1 and L2 genes of human papillomavirus type-33 in Cos-7 cells have been shown to efficiently incorporate polynucleotides (Unckell et al., 1997). The use of papillomavirus VLPs for delivering TRIM and/or TRAM containing polypeptides to cells would be particularly desirable for disrupting high risk E6 polypeptide interactions with CBP, Mdm2 or other TRAM-containing polypeptides since the VLPs would demonstrate a tropism similar to that of the natural papillomavirus infection.

The dose of substance used may be adjusted according to various parameters, especially according to the substance used, the age, weight and condition of the patient to be treated, the mode of administration used and the required clinical regimen. A physician will be able to determine the required route of administration and dosage for any particular patient and condition.

The invention will be described with reference to the following Examples which are intended to be illustrative only and not limiting. The Examples refer to the Figures. Referring to the Figures in more details:

FIGS. 1a–1d. E1A binds a 12 amino acid motif in CBP (amino acids 1811–1822).

Figure 1B:
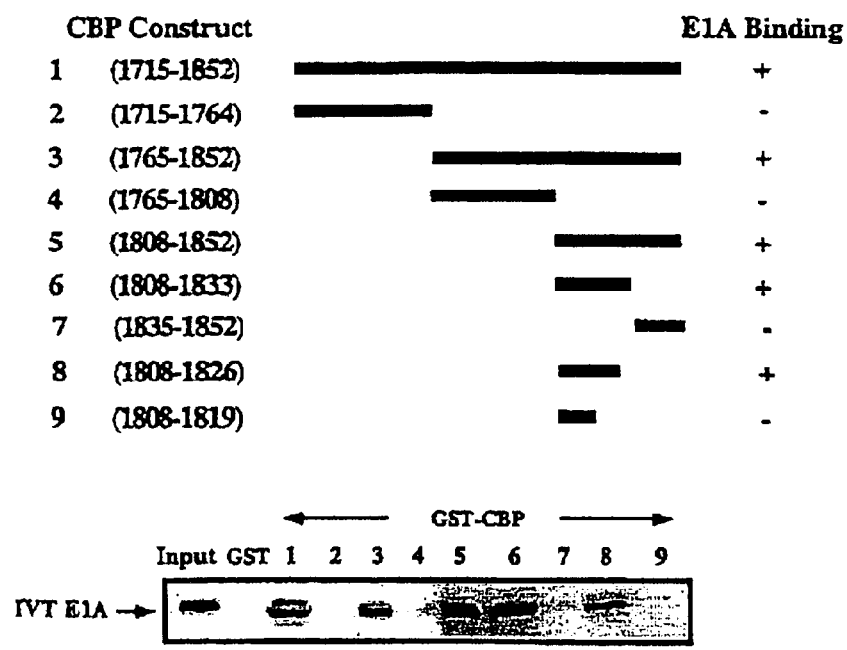
Figure 1C:
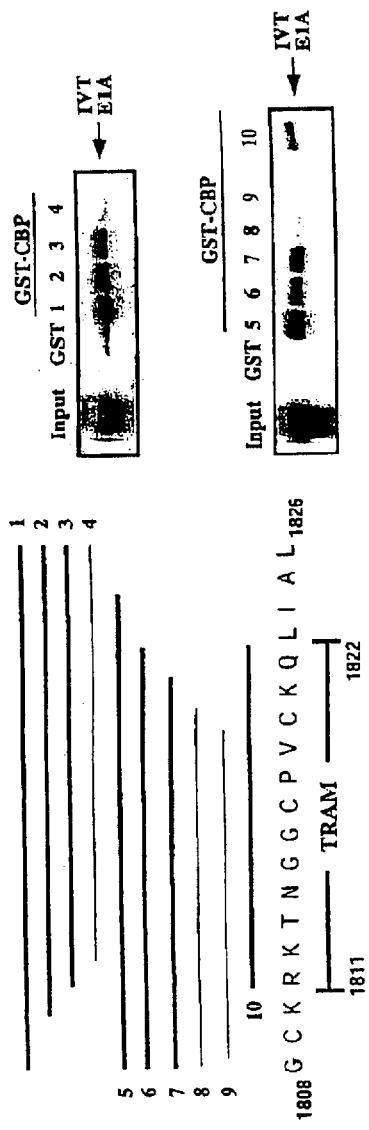
Figure 1D:
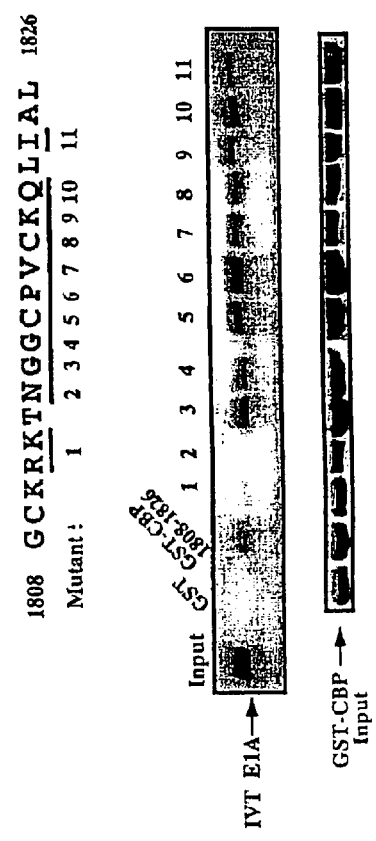

FIG. 1a, schematic representation of the transcription factor CBP showing an amino acid region (between 1621–1877) that binds the factors E1A, p53, E2F, and TFIIB. FIG. 1b, GST-CBP fusion constructs used in pull-down experiments to define sequences capable of binding 12S E1A. The bacterial GST-fusion proteins were bound to micro-columns and in vitro translated $^{35}$S-labeled E1A passed over them to detect protein-protein interactions (see methods). Approximately 10% of the E1A translation reaction was run in the input lane, GST represents a control column, and lanes 1 to 9 represent the eluate obtained after passing E1A over columns containing the nine GST-CBP fusion constructs. FIG. 1c, Further deletion analysis of CBP sequences 1808–1826. Thick lines indicate constructs that bind E1A, narrow lines those that do not. A minimal construct of 12 amino acids (construct 10, CBP 1811–22) still retains E1A binding activity. FIG. 1d, Mutagenesis of the CBP TRAM. Indicated are the eleven alanine substitutions used to determine amino acids required for the E1A interaction. All are single substitutions, except for mutant construct 1, which substitutes two basic residues. Pull-down experiments using wild-type or mutant GST-CBP (1808–1826) sequences were carried out and show that E1A binding is abolished by the R1811A, K1812A mutation and the N1814A mutation. Also shown is the amount of GST-CBP protein used in the pull-down experiment.

FIGS. 2a–2d. Identification of the amino acids in E1A involved in the interaction with CBP.

Figure 2A:
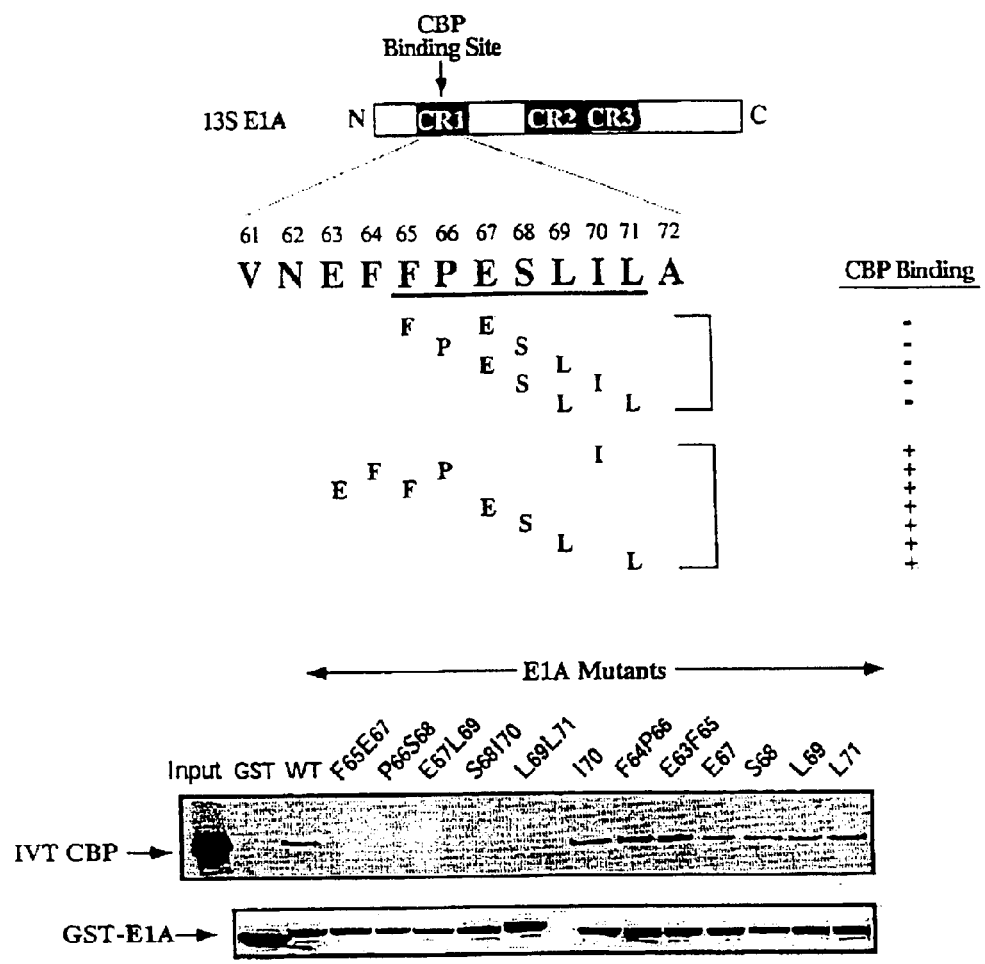

FIG. 2a, schematic representation of 13S E1A depicting conserved regions CR1, CR2, and CR3. Contained within CR1 are residues 63–67, previously implicated in the binding of CBP. GST-E1A proteins containing wild type or mutated (alanine substituted) sequences were tested for their ability to interact with $^{35}$S-labeled CBP (1621–1877). Shown are the results of these pull-down experiments along with a picture of a coomassie-stained SDS PAGE gel to show the quantities of GST-E1A fusion proteins recovered from the micro-columns. Double substitution mutants within sequences F65 to L71 fail to bind CBP. FIG. 2b, Peptide competition assays confirm the involvement of sequences F65 to L71 in the interaction with CBP. Peptides of 30 amino acids containing the sequences shown above were used in competition studies to test their ability to prevent the E1A-CBP interaction. Increasing amounts (0.1 mM, 0.5 mM, and 1 mM) of wild type peptide sequence (WT), or mutant sequences (Mut 1 or Mut 2) were used in E1A-CBP pull-down assays. Only the wild type peptide prevented the E1A-CBP interaction. FIG. 2c, p53, E2F, and TFIIB all bind to CBP sequences 1808–1826 that contain the TRAM. Binding can be inhibited by competition with a wild-type E1A peptide, but not by the Mut 2 E1A peptide. FIG. 2d, An alignment of E1A, p53, and E2F sequences with the conserved FXE/DXXXL TRAM interaction motif (TRIM) underlined.

FIGS. 3a–3d. Mdm2 contains a C-terminal TRAM that binds E1A, p53, E2F, and TFIIB.

Figure 3A:
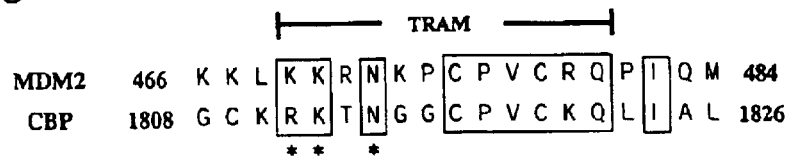
Figure 3B:
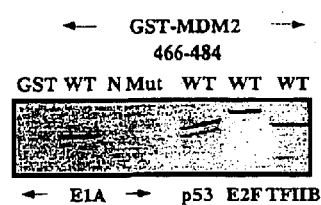
Figure 3C:
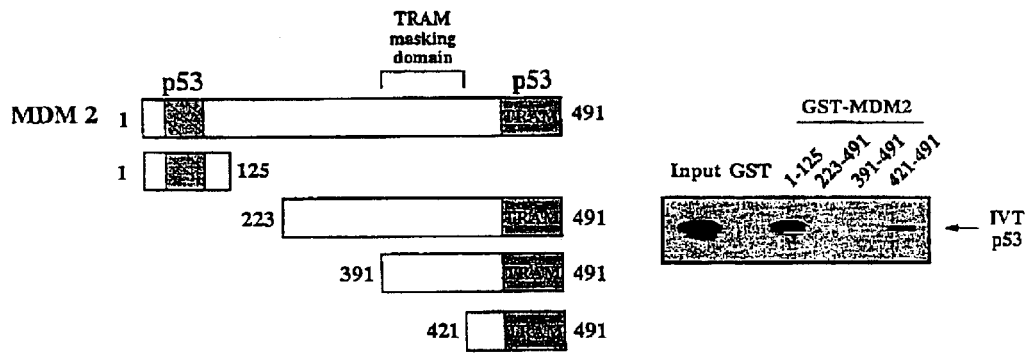
Figure 3D:
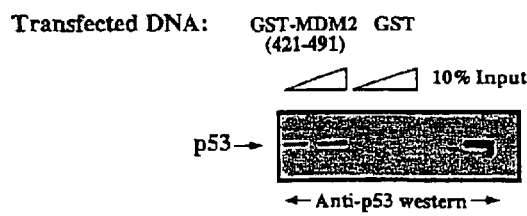

FIG. 3a, An alignment of sequences from human Mdm2 (466–484) and CBP (1808–1826). Conserved sequences are boxed and residues previously mutated (FIG. 1d) to prevent E1A interaction are denoted by an asterisk. FIG. 3b, In vitro binding of E1A, p53, E2F, and TFIIB to the Mdm2 TRAM. Pull-down experiments show all four in vitro translated and radiolabeled proteins bind the wild type Mdm2 TRAM contained within sequences 466–484. A mutant GST-Mdm2 construct (N472A) fails to bind E1A, like its CBP counterpart (FIG. 1d). FIG. 3c, The C-terminal Mdm2 TRAM is masked by N-terminal sequences between 391–421. Shown is a schematic representation of full-length Mdm2 containing the N- and C-terminal regions capable of binding p53, along with constructs used in in vitro pull-down experiments. GST-Mdm2 fusion constructs containing Mdm2 sequences 223–491 and 391–491 show vastly reduced binding capabilities compared to the unmasked C-terminal region 421–491. Also shown for comparison is the use of the N-terminal 1–125 amino acid region of Mdm2, previously shown to interact with both p53 and E2F. FIG. 3d, In vivo interaction between Mdm2 C-terminal sequences (421–491) containing an unmasked TRAM, and p53. MRC5.SV40 cells were transfected with 0.1 µg or 0.5 µg of either a pCMV-GST-Mdm2 (421–491) construct, or a control CMV-GST construct. After 48 hours, cell lysates were prepared from these cells and incubated with glutathione-Sepharose beads, then subjected to washes and elution as described for in vivo pull-downs (see methods). Eluted proteins were run on SDS polyacrylamide gels and subjected to standard western blot analysis using the p53 monoclonal antibody DO-1. (Santa Cruz). Lysate containing transfected GST-Mdm2 (421–491) indicated complex formation between p53 and Mdm2 (421–491), while those from the GST control transfections failed to pull-down p53 protein. Lysate approximating to 10% of the amount loaded onto microcolumns was loaded directly onto the same SDS polyacrylamide gel and subjected to the same western blot analysis. A comparison between p53 levels detected suggests that approximately 2–3% of total cellular p53 is complexed with the GST-Mdm2 fusion protein.

FIGS. 4a–4d. The CBP and Mdm2 TRAMs compete for p53 binding with the N-terminal domain of full-length Mdm2 and activate p53-dependent transcription.

Figure 4A:
Figure 4B:
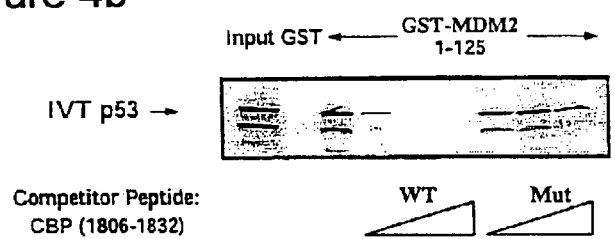
Figure 4C:
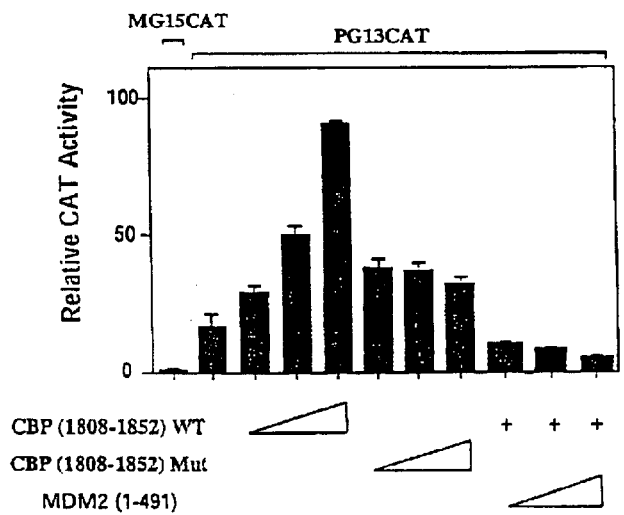
Figure 4D:
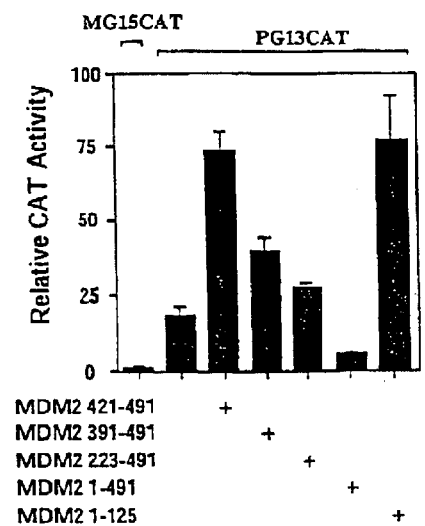

FIG. 4a, Differential effect of the p53 mutant 14/19 on the Mdm2 N-terminal domain and the CBP and Mdm2 TRAMs. In vitro translated $^{35}$S-methionine labelled p53, either wild type or harbouring the L14Q/F19S mutation, were analysed for their ability to bind to GST-fusion proteins containing the N-terminal Mdm2 domain (1–125), the CBP TRAM (1715–1852), or the Mdm2 TRAM (421–491) in pull-down assays. While the binding of p53 to the N-terminal domain of Mdm2 is drastically affected by the 14/19 mutation, neither the CBP nor the Mdm2 TRAMs are affected. FIG. 4b, A CBP TRAM peptide can inhibit the binding of the N-terminal Mdm2 domain to p53. CBP peptides of 27 amino acids (1806–1832) containing either wild type or mutant (R1811, K1812, N1814) TRAM sequences were used in competition assays to prevent the interaction of in vitro translated p53 and GST-Mdm2 (1–125). Wild type peptide was able to completely inhibit the p53-Mdm2 interaction over the range used (10–100 μM), while the ability of mutant TRAM peptide to inhibit the interaction was severely impaired. FIG. 4c, CBP sequences containing a wild type TRAM activate p53-dependent transcription. Transient transfection of U-2 OS cells was carried out using either 2 μg of a p53-responsive reporter gene (PG13CAT) or a control vector (MG15CAT). Also indicated is the co-transfection of 1, 2 or 4 μg of a CMV-GST-CBP (1808–1852) vector containing either a wild type TRAM, or a mutant TRAM (R1811A, K1812A). Introduction of the wild type TRAM resulted in a dose-dependent increase in p53-dependent transcription. This level of activation was not obtained when the mutant TRAM construct was used. The co-transfection of full-length Mdm2 abolished TRAM activation of p53 by CBP. FIG. 4d, U-2 OS transfection experiments demonstrate that introduction of unmasked Mdm2 TRAM sequences result in a similar activation of p53-dependent transcription. In addition to PG13CAT, co-transfections were carried out using 2 μg of the CMV-GST-Mdm2 expression vector (containing Mdm2 sequences 421–491, 391–491, 223–491, 1–491, or 1–125). It can be seen that transcription from the p53-dependent reporter construct is activated upon co-transfection of the Mdm2 421–491 construct that contains a functional TRAM. This effect is reduced upon the inclusion of N-terminal masking sequences (see 391–491 and 223–491). Co-transfection of the N-terminal motif of Mdm2 alone also activated p53-dependent transcription, while full-length Mdm2, containing sequences that lead to p53 degradation, resulted in a reduction in p53-dependent reporter activity.

Figure 5A:
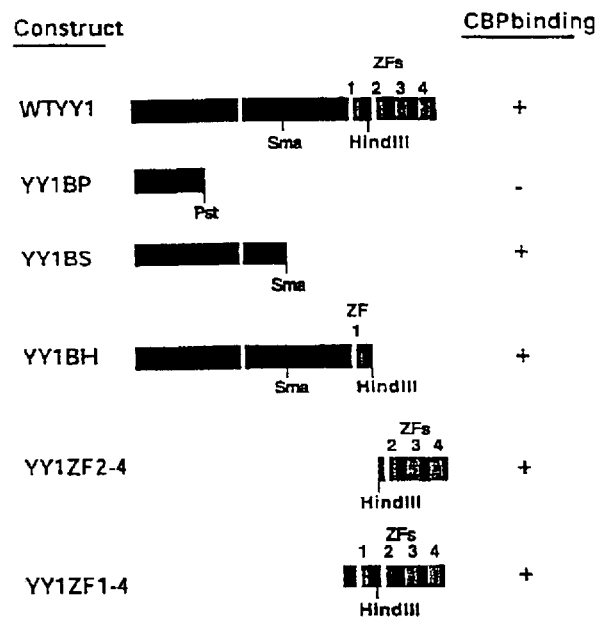
Figure 5B:
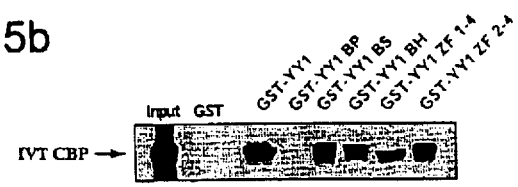
Figure 5C:
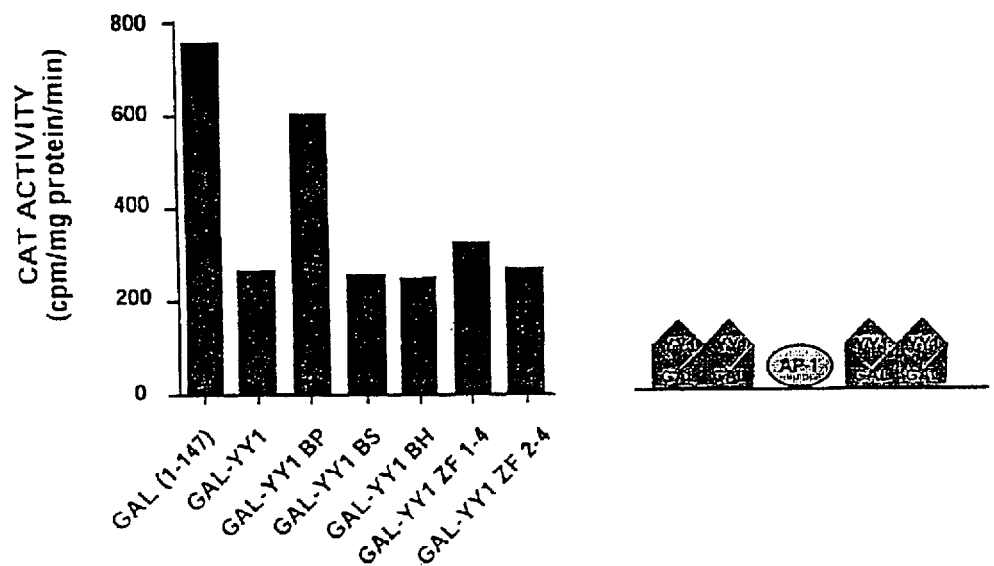

FIGS. 5a–5c. YY1 fragments containing sequences showing marked similarity to previously defined TRIMs are able to interact with CBP in vitro and are capable of repressing AP-1 activity in vivo.

FIG. 5a, Schematic representation of the YY1 constructs used in in vitro pull-down assays and in in vivo repression assays. WTYY1 represents the full-length wild type YY1 sequence, YY1BP, YY1BS, and YY1BH, start at amino acid position 1 and terminate at unique restriction sites within the YY1 sequence, while YY1ZF 2–4 and 1–4 represent PCR amplified YY1 sequences containing either all 4 zinc fingers (ZF 1–4) or the last 3 zinc fingers (2–4). These sequences were either fused to GST or GAL4 (1–147) sequences for the assays described below. FIG. 5b, In vitro pull-down assays demonstrate the ability of fragments containing at least one putative TRIM sequence to interact with IVT CBP (1621–1877), while the fragment YY1BP which does not contain a TRIM sequence, fails to interact with CBP. FIG. 5c, YY1 fragments capable of binding CBP in vitro demonstrate an ability to repress AP-1 activity in vivo. The schematic drawing shows the two palindromic GAL4 binding sites that were used to replace naturally occuring YY1 sites in the p80:2e/9e CAT reporter construct (O'Connor el al., 1996). This p80:2e/9eGAL reporter construct was then co-transfected with plasmids capable of expressing GAL-YY1 fusion proteins under the direction of an SV40 promoter in primary human keratinocytes. It can be seen that the expression of GAL-YY1 fusion constructs containing TRIMs results in a repression of CAT activity compared to those results obtained when only GAL sequences are co-transfected. By contrast the co-tranfection of a GAL-YY1BP construct which possess no TRIM fails to show any significant repression of CAT activity FIGS. 6a–6b. Differential binding properties of CBP TRAM mutant sequences to TRIM containing proteins.

FIG. 6a, A sequence alignment of previously defined TRIMs along with the putative TRIM sequences present in TFIIB, YY1 and MyoD. The phenylalanine residue and acidic residue in postions 1 and 3 respectively are highly conserved, while the leucine residue in the $7^{th}$ position sometimes shows a conservative change with another neutral, non-polar amino acid residue. Also illuminated is the large variation in amino acid residue composition in the remaining TRIM sequences, and in the surrounding sequences. FIG. 6b, In vitro pull-down assays demonstrate the failure of TRAM C-terminal residue alanine substitutions to bind a subset of TRIM-containing proteins.

FIGS. 7a–7d. HPV-16 E6 interacts with the transcriptional co-activator CBP/p300. (FIG. 7a) Equal amounts of partially purified full-length (FL) CBP/p300 from HeLa nuclear extract was passed over GST, GST-16E6, GST-P/CAF, and GST-YY1 micro-affinity columns (see Materials and Methods). After SDS-gel electrophoresis and transfer to membranes, western analysis detected the presence of CBP/p300. (FIG. 7b) GST micro-affinity columns were used to detect the interaction of in vitro translated and radiolabeled HPV-16 E6 with GST-CBP II (residues 1621 to 1877). No interaction was detected for the control GST-column or the GST-CBP I (residues 461 to 662) column. (FIG. 7c) Comparison of the HPV-16 E6-CBP II interaction with known E1A-CBP II and HPV-16 E6-E6AP interactions using GST micro-affinity column assays. (FIG. 7d) Demonstration of a direct interaction between HPV-16 E6 and CBP using two recombinant bacterially expressed proteins. GST or GST-E6 was passed over a column containing MBP-CBP (residues 1808–1852) fusion protein. Bound GST-fusion protein was detected by western analysis using a specific GST antibody. The MBP-CBP fusion protein was also passed over a GST or GST-E6 column and the interaction detected using an MBP antibody.

Figure 8:
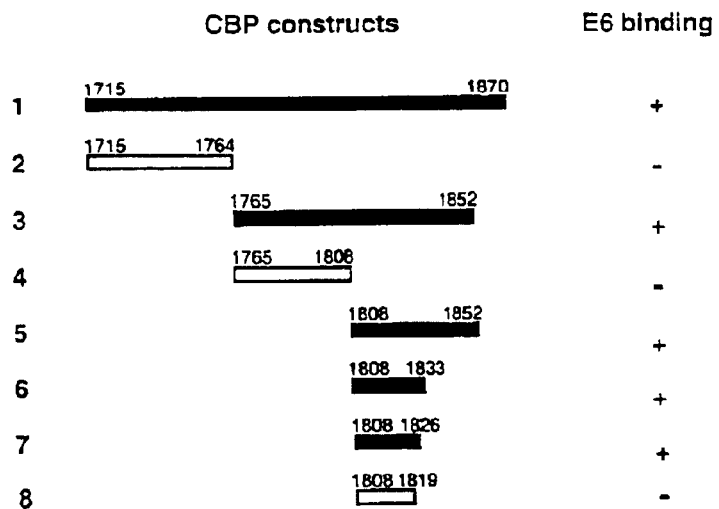
Figure 8:
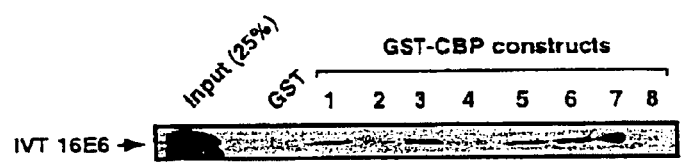
Figure 8:
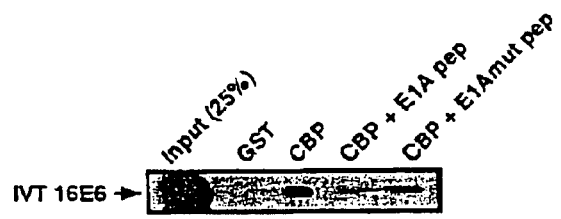

FIG. 8. Identification of an HPV-16 E6 binding site on CBP/p300. Shown is a schematic representation of GST-CBP fusion constructs used in micro-affinity column experiments used to define CBP sequences capable of binding HPV-16 E6. Demonstrated is the ability of a 19 amino acid sequence of CBP (residues 1808–1826) to bind in vitro translated HPV-16 E6 protein (lane 7). Deletion into these sequences abolishes E6 binding (lane 8). Also shown is an alignment of the identified E6-binding site within CBP and a comparison with the corresponding p300 sequence. An asterix represents the conservation of an identical amino acid residue in that position, while a "+" represents a conservative change. An E1A peptide that can bind this 19 amino acid CBP sequence can inhibit the E6-CBP interaction, while a CBP-binding deficient mutant peptide cannot.

Figure 9A:
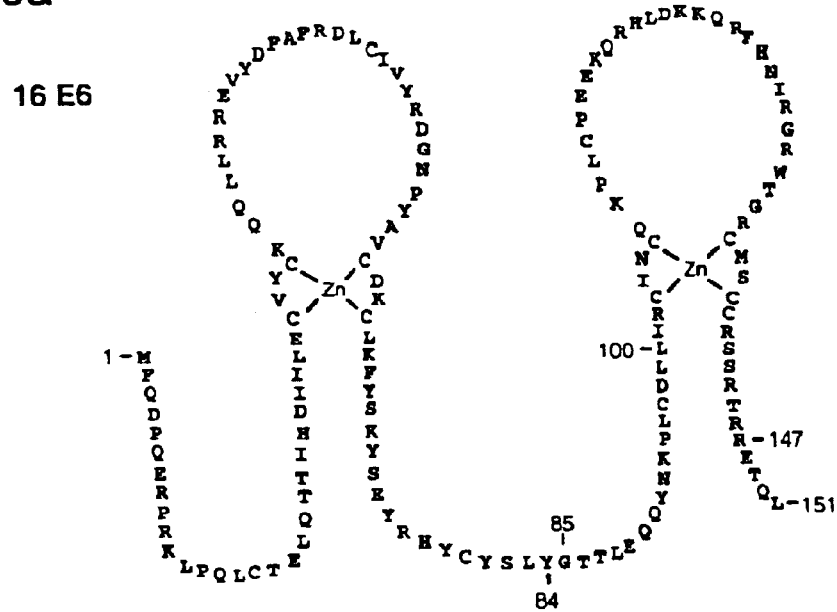
Figure 9B:
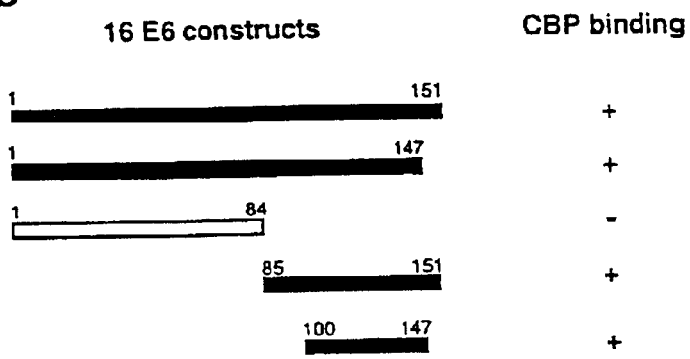
Figure 9C:
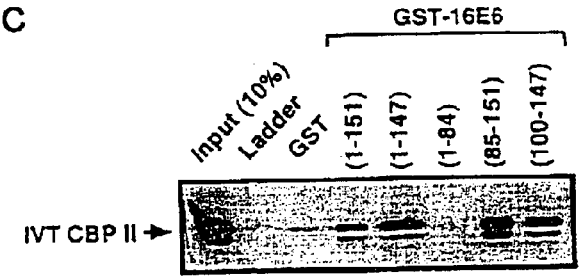

FIGS. 9a–9c. Mapping of an HPV-16 E6 region involved in the interaction with CBP. (FIG. 9a) Amino acid sequence of the HPV-16 E6 protein indicating the two zinc finger structures present in this protein. Indicated are the numbers of the amino acid residues which mark start or end points of HPV-16 E6 fragments used in interaction studies. (FIG. 9b) Schematic representation of GST-E6 fusion constructs used in micro-affinity column assays. (FIG. 9c) Interaction experiments define a region between HPV-16 E6 residues 100–147 as sufficient for the binding of CBP.

Figure 10A:
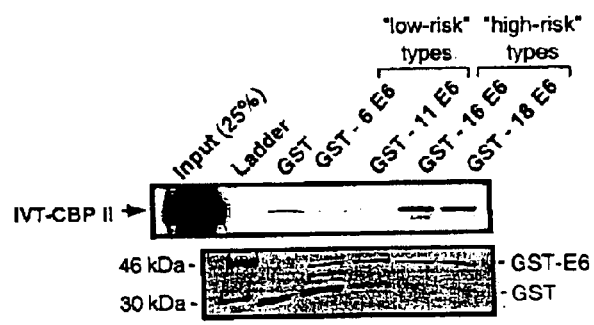
Figure 10A:
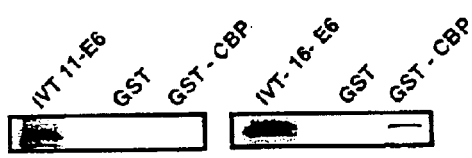
Figure 10B:
Figure 10B:
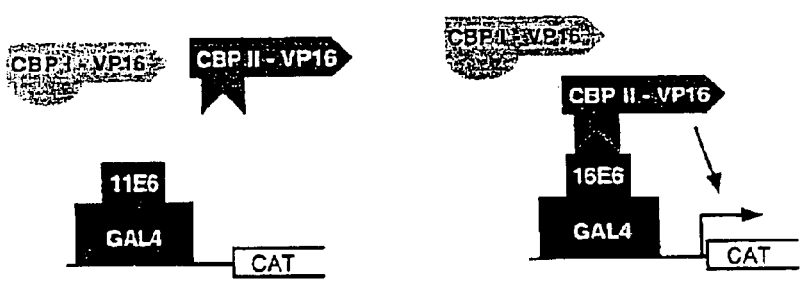
Figure 10B:
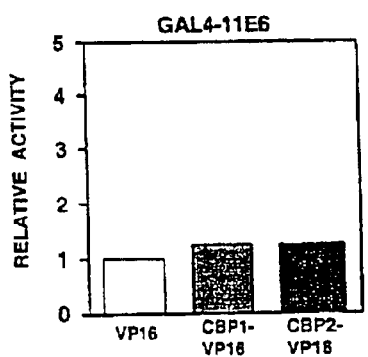
Figure 10B:
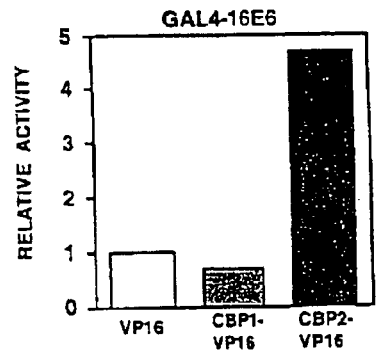

FIGS. 10a and 10b. The E6-CBP/p300 interaction is specific for "high-risk" HPV E6 proteins. (FIG. 10a) Micro-affinity column experiments using either GST-fusion or in vitro translated E6 proteins demonstrate that only E6 proteins from the high-risk HPV types 16 and 18, but not the low-risk HPV types 6 and 11, are capable of interacting with CBP. (FIG. 10b) Mammalian two-hybrid experiments (described in Material and Methods) and shown schematically here, indicate that the distinction between high-risk and low-risk E6 proteins extends to the in vivo interaction with the CBP II domain. Activation of the G5E1BCAT reporter is only seen after co-transfection of GAL4-16 E6 and CBP II-VP16, and not for those experiments in which GAL4-11 E6 or CBPI-VP16 proteins were expressed.

Figure 11A:
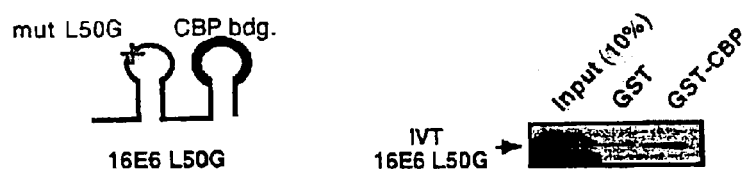
Figure 11B:
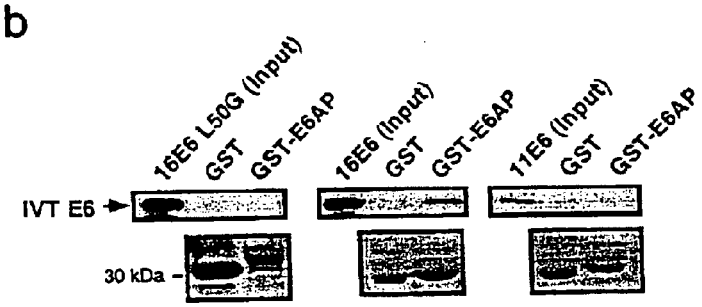
Figure 11C:
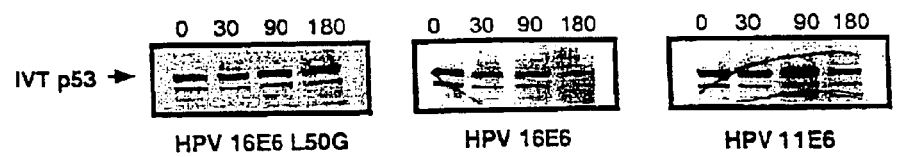

FIGS. 11a–11c. The HPV-16 E6 mutant L50G binds CBP, but is unable to interact with E6AP or degrade p53 in vitro. (FIG. 11a) Schematic representation of the HPV-16 E6 mutant L50G showing the position of the amino acid exchange in the first zinc finger (marked by a +) and the identified CBP-interaction domain within the second zinc finger (bold line). GST micro-affinity column experiments using in vitro translated HPV-16 E6 L50G protein demonstrate the ability of this mutant to interact with GST-CBP. (FIG. 11b) Similar in vitro micro-affinity column experiments show that unlike the WT 16 E6 protein, but similar to HPV-11 E6, the HPV-16 E6 mutant L50G is unable to interact with GST-E6AP. (FIG. 11c) p53 degradation assays using in vitro translated $^{35}$S-labeled p53 mixed with various in vitro translated E6 proteins. The numbered columns indicate the levels of p53 protein after various incubation times (0, 30, 90, and 180 min) at room temperature.

Figure 12A:
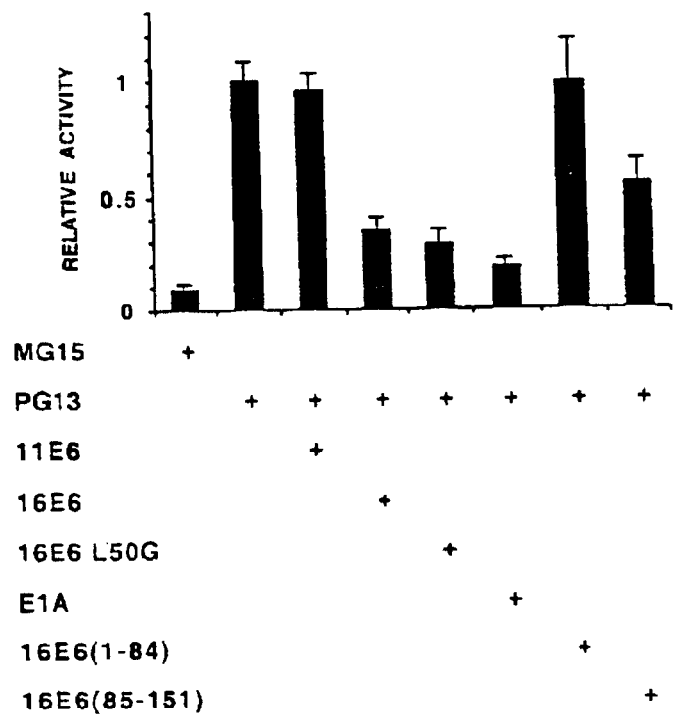
Figure 12B:
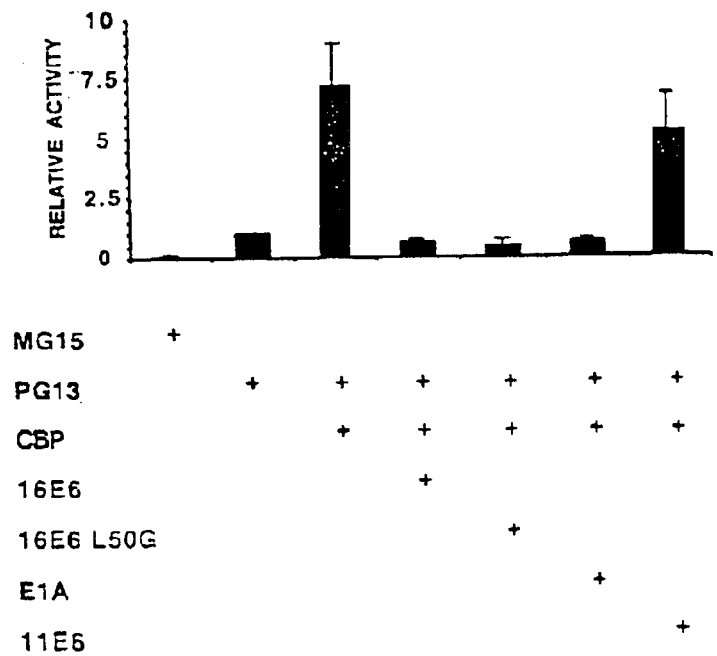

FIGS. 12a and 12b. HPV-16 E6 targets the ability of CBP to activate p53-dependent transcription. (FIG. 12a) U2-OS cells were transfected with the p53-responsive CAT reporter (PG13) or a control vector with mutated p53 binding sites (MG15). Co-transfection of expression-vectors for viral proteins show that HPV proteins able to interact with CBP can down-regulate p53 transactivation to a level comparable with Ad E1A. (FIG. 12b) Over-expression of full-length CBP in experiments similar to those described above show that HPV proteins able to interact with CBP, including the HPV-16 L50G mutant, abolish the CBP-dependent superactivation of p53-dependent transcription seen with full-length CBP alone.

FIG. 13. Polylinker of pMALP.

EXAMPLE 1

Materials and Methods

Plasmids and fusion proteins. GST-CBP, GST-Mdm2, or GST-E1A constructs were obtained by cloning PCR amplified fragments or double stranded oligonucleotides into pGEX2TK (Pharmacia). The GST-Mdm2 (1–125) construct was a gift from Benjamin Li. GST-fusion proteins were expressed in E. coli, extracted with lysis buffer (50 mM Tris-HCl pH 8.0, 0.5 mM EDTA, 5 mM DTT, 15% glycerol, 1 mg/ml lysozyme and 1 mM PMSF), and after sonication and centrifugation, stored at −70° C. CMV-GST construct pXJGST was a gift from Edward Manser and was constructed by inserting GST sequences into the EcoRI/BamHI sites of pXJ40 (Xiao et al., 1991). CBP and Mdm2 sequences were then cloned into this vector via the BamHI HindIII sites.

In vitro pull-down assays using glutathione-Sepharose micro-columns. Bacterial lysate containing GST-fusion protein was incubated with glutathione-Sepharose beads (Pharmacia) for 30 min at 4° C. in 1×NENT buffer (100 mM NaCl, 1 mM EDTA, 0.5% NP-40, Tris-HCl, pH 8.0). After spinning down and washing with 1 ml 1×NENT, the beads were loaded into a yellow Gilson pipette tip containing a glass bead (BDH, cat. no. 332134Y) to create a 25 µl GST micro-column. In vitro transcription and translation of proteins incorporating $^{35}$S-methionine was performed using TNT kits (Promega) according to the manufacturer's recommendations. 40 µl of a 50 µl IVT reaction was diluted with 360 µl of IPD buffer (50 mM KCl, 40 mM Hepes, pH 7.5, 5 mM 2-β mercaptoethanol, 0.1% Tween-20, 0.5% milk) before being passed down the GST micro-column. After washing the column twice with 1 ml wash buffer (IPD buffer containing 150 mM KCl), proteins were eluted from the column by adding 25 µl of 2×SDS loading dye, heating to 95° C. for 5 min, chasing with 25 µl water, and spinning in a micro-centrifuge. Approximately half of the sample was then loaded onto a SDS polyacrylamide gel and, after running, staining, and de-staining, the gels were treated with Enlightning (NEN Research Products) for 30 min before drying and exposure to autoradiographic film.

Peptide competition assays. To study the influence of specific peptides on protein-protein interactions in pull down experiments, GST-fusion proteins were bound to glutathione-Sepharose as described previously. In the case of E1A peptide competition, the washed beads were incubated in 200 µl IPD buffer containing peptide (final concentration 10 µM–100 mM), and rotated at 4° C. for 1 hour. 40 µl of an in vitro translation reaction was then diluted with 60 µl IPD buffer and added to the sample before incubating for a further 30 min at 4° C. For the CBP TRAM peptide competition studies, the peptide was pre-incubated with diluted in vitro translation reaction for 15 min at 4° C. before incubation with the GST-fusion protein. After spinning down and washing the glutathione-Sepharose beads, proteins were eluted in 50 µl 1×SDS sample buffer by heating the beads to 95° C. for 5 min. Approximately half of the sample was then run on SDS polyacrylamide gels and treated as described above.

Detection of in vivo interactions between GST-Mdm2 proteins and endogenous p53. MRC5.SV40 cells were transiently transfected with 0.1 µg–2.0 µg of CMV-GST constructs using lipofectin reagent (Gibco-BRL). After 48 hours, cells were harvested and resuspended in MCL Buffer (50 mM Tris.Cl pH 7.6, 1 mM EDTA, 1 mM DTT, 50 mM NaF, 0.3M NaCl, 0.1×Protease inhibitor cocktail (Sigma), 1.5 mM PMSF). Cells were then lysed by sonication and cell debris pelleted by ultracentrifugation. The extent of GST and GST-Mdm2 protein expression was determined for each lysate by western blot analysis using anti-GST antibody B-14 (Santa Cruz). Lysate containing approximately equal amounts of GST or GST-Mdm2 protein (usually around 500 µg) was then mixed with glutathione-Sepharose beads in 400 µl of IPD buffer and incubated for 1 hour at 4° C. GST-fusion proteins, along with interacting proteins, were purified by spinning down the glutathione-Sepharose beads and washing twice with 1 ml of wash buffer. Remaining proteins were eluted in 50 µl 1×SDS sample buffer by heating the beads to 95° C. for 5 min. The presence of p53 was detected by standard western blot analysis using the anti-p53 monoclonal antibody DO-1 (Santa Cruz).

Transfections and CAT assays. U-2 OS cells or MRC5.SV40 cells (a gift from Dr. Peter Karran) were plated onto 10 cm-diameter culture dishes and transfected at 50–70% confluency using lipofectin reagent (GIBCO-BRL) as described previously (O'Connor et al., 1996). Chloramphenicol acetyl transferase (CAT) assays have also been described previously (O'Connor et al., 1996) and the data presented represents between three and ten independent transfection experiments.

Results

Identification and Characterisation of a 12 Amino Acid Motif in CBP (TRAM) that Binds E1A Previously published work has shown that a 257 cystein-rich amino acid region of CBP spanning amino acids 1621–1877 could bind E1A, TFIIB, P/CAF, c-fos and MyoD, as well as a number of other transcription factors. Using glutathione-sepharose micro-columns and a series of GST-CBP fusion proteins we initially identified a 19 amino acid region of CBP (1808–1826) that was sufficient for the binding of E1A (FIG. 1b). Deletion into this region abolished E1A binding (FIG. 1b, lane 9).

Further fine deletion analysis of CBP (1808–1826) identified a 12 residue sequence (1811–1822) which is sufficient for E1A binding (FIG. 1d), although this sequence binds with slightly reduced affinity compared with the larger, 19 residue (1808–1826) sequence. We have termed the sequence between 1811–1822 a TRanscriptional Adaptor Motif (TRAM).

To establish the residues important for TRAM function we carried out a mutagenesis analysis. All except one of the residues within the CBP TRAM were mutated to alanine. FIG. 1d shows that only two mutations drastically affect the binding to E1A: a pair of basic residues (RK, 1811/1812) and an asparagine residue (N 1814) at the N-terminus of the motif. The fact that no other residue had a dramatic effect on E1A binding suggests that the C-terminus of this motif provides a lower contribution to affinity under the conditions used. Nevertheless the deletion analysis in FIGS. 1b and 1c clearly show that these C-terminal residues are required for binding.

Identification of a TRAM Interaction Motif (TRIM) in E1A, Required for the Binding of the CBP TRAM Having identified the E1A-binding region of CBP, we were interested in identifying the residues in E1A responsible for binding the CBP TRAM. Previous dissection of E1A has implicated residues 63–67 in binding to this region of CBP. We therefore carried out an extensive mutagenic analysis to establish the motif in E1A required to bind CBP. FIG. 2 shows that the sequence FPESLIL can be defined as essential for the binding to CBP (1621–1877). Mutagenesis of any two residues within this sequence (FE, PS, EL, SI or LL) abolishes binding to CBP. However, single residue substitutions in this motif are insufficient to disrupt the E1A-CBP complex, indicating that the interaction between these proteins is reliant on a combination of residues.

Peptide competition studies confirmed these results. Peptides containing wild type or mutant E1A sequences were analysed for their ability to prevent the binding of full-length radiolabeled 12S E1A protein to a GST-CBP fusion protein (FIG. 2b). While E1A binding was detected in the absence of competitor peptide, increasing amounts of wild type E1A peptide abolished the interaction. By contrast, peptides containing mutations in E67L69 (peptide Mut 1), or additionally F65L71 (peptide Mut 2), failed to abolish the E1A-CBP interaction. These results demonstrate that the interaction of E1A with the CBP TRAM is via a small E1A motif.

Transcription Factors p53, E2F and TFIIB Interact with CBP Via its TRAM

The CBP TRAM is within a region of CBP (1621–1877) which is a "hot spot" for the binding of transcription factors (FIG. 1a). We therefore asked whether the TRAM was the target of these interactions. FIG. 2c shows that three transcription factors, p53, E2F and TFIIB, which bind this region of CBP, interact with the CBP TRAM (GST-CBP 1808–1826). The interaction can be competed with an E1A peptide containing the wild type CBP binding site, but not with a mutant E1A peptide that is unable to bind CBP (Mut 2).

Identification of a Conserved TRIM Sequence in p53 and E2F

Given that E1A, p53, E2F and TFIIB recognise the same motif within CBP, it is quite likely that these proteins contain a conserved domain through which the interaction is mediated (a TRAM-Interaction Motif (TRIM)). Previous mutagenesis studies have defined residues in two transcription factors, p53 and E2F, which are necessary for the interaction with CBP. FIG. 2d shows that these residues of p53 and E2F show marked similarity to the CBP binding site in E1A. A conserved motif FXE/DXXXL is present in all three proteins, which when mutated eliminates CBP binding. Thus, the results in FIG. 2 provide a model in which E1A regulates the activity of certain CBP-binding proteins by possessing a motif used by these cellular transcription factors to bind CBP.

Identification and Characterisation of a TRAM Sequence in the C-terminus of Mdm-2 that Binds TRAM-interacting Proteins A computer-based search of other proteins which may contain a TRAM revealed a high degree of similarity between. CBP residues 1811–1822 and a sequence at the C-terminus of the Mdm2 protein (FIG. 3a). The conservation overlaps precisely the TRAM sequence of CBP, as defined by the deletion analysis in FIG. 1. In addition, the residues found to be important for the protein-protein interaction functions of the CBP TRAM (RK 1811/1812 and N 1814) are conserved in the Mdm2 TRAM sequence. Significantly, the Mdm2 TRAM also has the capacity to bind the same proteins, namely E1A, p53, E2F, and TFIIB that contact the CBP TRAM (FIG. 3b). A mutant GST-Mdm2 construct (N472A) fails to bind E1A, like its CBP counterpart (FIG. 1d). Thus, in the context of another transcriptional regulator, Mdm2, a TRAM sequence mediates interaction to a similar set of transcription factors. This binding is independent of the N-terminal sequences in Mdm2 that have previously been shown to bind p53 and E2F.

Mdm2 Binds to p53 Via an Mdm-2 C-terminal TRAM

The Mdm2 protein is an important regulator of p53 activity. Binding of Mdm2 through the N-terminal domain to p53 results in the repression of p53 transactivation capacity, and also leads to the degradation of the p53 protein. Previous dissection of Mdm2 has not identified a p53-binding site at the Mdm2 C-terminus. FIG. 3c shows that this is most likely due to the fact that the TRAM at the C-terminus of Mdm2 is masked in vitro by sequences N-terminal to it. Thus, the Mdm2 C-terminus 421–491 is able to bind p53, but N-terminally extended peptides (223–491 and 391–491) do not. Consistent with previous observations, the N-terminus of Mdm2 (1–125) also binds p53. This masking effect of the C-terminal Mdm2 TRAM was also seen for E2F (data not shown), suggesting that it is not restricted to p53 alone.

To confirm that the TRAM of Mdm2 was able to recognise p53 in vivo, we introduced a CMV-GST-Mdm2 (421–491) expression vector into MRC5.SV40 cells. FIG.

3d shows that purification of the GST-Mdm2 fusion protein (but not GST alone) from these cells results in the co-purification of endogenous p53, as detected by the p53-specific DO-1 antibody. Thus the TRAM-containing C-terminus of Mdm2 represents an independent binding site for p53 in vivo. The relative contribution of the N- and C-terminal binding sites for p53 in the context of full-length protein is unclear at this stage. However the in vitro data presented here raise the possibility that the TRAM sequence of Mdm2 may be unmasked only under certain physiological conditions.

Inspection of the masking region from 391–421 shows that a number of SQ or TQ motifs are present. These sites have been shown to represent potential phosphorylation sites for DNA-dependent protein kinase (DNA-PK). This kinase is activated in response to DNA damage. Given the important role p53 plays in cell cycle arrest and apoptosis after DNA damage, it is tempting to speculate that phosphorylation of SQ/TQ motifs in the Mdm2 C-terminal could result in an unmasking of the Mdm2 TRAM.

The N-terminal domain of Mdm2, and the CBP and Mdm2 TRAMs, recognise the same region of p53. FIG. 4a demonstrates that while a previously described p53 mutation (L14Q F19S) drastically affects the binding of the N-terminal domain, it does not affect the binding of the CBP or Mdm2 TRAMs. This suggests that the importance of individual amino acid residues, and therefore the contacts involved, differ in these two types of protein interaction motif.

To determine whether or not the binding of the N-terrninal Mdm2 domain and TRAMs to p53 was mutually exclusive, we carried out a competition assay in which a p53-Mdm2 (1–125) interaction was challenged with either a wild type CBP TRAM-containing peptide (1806–1832) or a peptide containing a mutated TRAM sequence. FIG. 4b shows that the wild-type peptide successfully competes with the N-terminal Mdm2 domain for p53 binding, while the mutant TRAM peptide's ability to compete is significantly reduced.

TRAM Sequences Activate p53-dependent Transcription

In a recent report, disruption of the Mdm2 N-terminal-p53 interaction resulted in a striking accumulation of endogenous p53 protein, activation of p53-dependent transcription, and cell cycle arrest. The results presented in FIG. 4b suggested to us that the introduction of rRAM-containing proteins into cells containing functional p53 and full-length Mdm2 would result in a similar effect. Transient transfection experiments using U-2 OS cells show that the introduction of CBP sequences (1808–1852) containing a functional TRAM do indeed result in an activation of p53-dependent transcription in a dose-dependent manner (FIG. 4c). The presence of a TRAM mutation significantly reduces this effect. Moreover, the activation of p53-dependent transcription by these CBP sequences is abolished after the co-transfection of full-length Mdm2, which is consistent with the idea that these proteins may be competing for p53 binding in vivo.

FIG. 4d illustrates that the ability to activate p53-dependent transcription is not limited to the CBP TRAM, but can also be achieved using Mdm2 C-terminal sequences containing a functional TRAM. Activation was significantly reduced when N-terminal "masking" sequences (391–491 and 223–491) were included, suggesting that masking of the Mdm2 TRAM occurs in vivo as well as in vitro. The transfection of the N-terminal Mdm2 domain (1–125), which contains p53-binding sequences but not those implicated in p53 degradation, also resulted in a comparable activation of p53-dependent transcription.

The three constructs that activate p53-dependent transcription, CBP (1808–52), Mdm2 (421–91), and Mdm2 (1–125), share no obvious common feature other than their ability to bind p53. This strongly suggests a model in which these proteins compete for p53 binding with the N-terminal domain of full-length endogenous Mdm2, resulting in an abrogation of Mdm2-mediated p53 degradation.

In summary, our results show that both CBP and Mdm-2 contain a transcriptional adaptor motif that recognises multiple cellular regulators, at least some of which such as E2F and p53 contain an E1A-like TRIM having the consensus FXE/DXXXL motif. Both TRAMs share an ability to activate p53 function by competing with the N-terminal motif of full-length Mdm2 for p53 binding. Competition between proteins that contain the FXE/DXXXL motif and TRAMs may also play an important role in the regulation of many different signal transduction pathways, and evidence obtained from the study of adenovirus E1A suggests that viruses can manipulate these protein-protein interactions to alter cell fate. This simple, motif-based interaction interface should therefore provide a good target for drug-based therapeutic intervention.

The Transcriptional Regulator YY1 Contains Multiple TRIMs that Correlate with CBP Binding and in vivo Repressioln Yin Yang 1 (YY1) is an important regulator of numerous viral and cellular genes. Recently, we have shown that YY1 can repress AP-1 mediated activation of the HPV-16 E6/ E7 promoter. Both the jun and fos family members that make up the AP-1 transcription factor have been shown to use CBP as a co-factor during transcriptional activation. We have previously shown that YY1 can interact with CBP, while others have demonstrated the ability of YY1 to interact with p300.

An examination of the YY1 sequence reveals the presence of three potential TRIMs (127–133; 307–313 and 334–340). In FIG. 5a YY1 fragments used in in vitro binding studies and in vivo transcription repression studies show the positions of the three TRIMs (white bars), one of which is in the N-terminal half of the protein, the others being in the C-terminal portion as part of zinc finger structures. FIGS. 5b and 5c demonstrate a correlation between YY1 constructs containing E1A-like TRIMs, CBP binding, and the ability to repress AP-1 activity in vivo. These results suggest that a TRIM-TRAM interaction may play a role in the modulation of gene expression by a DNA-binding factor.

In many cases YY1 serves to keep viral gene expression at low levels until a particular trigger or phase in the viral life cycle when relief of YY1 repression occurs, often mediated by other transcription factors. It may be possible therefore, to use TRIM-TRAM interactions to down-regulate specifically viral gene expression in an analogous way.

Differential Binding of TRAM Variants to TRIM-containing Proteins

The E1A, p53 and E2F TRAM interaction motifs (TRIMs) studied initially consisted of the consensus FXE/DXXXL. A study of potential TRIMs from other proteins suggests that in addition to the variation in the $7^{th}$ position (in which an alternative, neutral, non-polar amino acid may substitute for leucine), there is also significant variation within the residues denoted by 'X' (see FIG. 6a). Since the composition of residues within the TRIM could influence the contacts made with any given TRAM, we were interested to see if different TRAM variants demonstrated differential binding to a number of these TRIM-containing proteins.

We used the eleven alanine substitution mutants, previously created in the context of the GST-CBP (1808–1826)

fusion protein, in pull-down assays with p53, TFIIB, and YY1. It can be seen from FIG. 6b that as well as being affected by the mutations in R1811/K1812 (mutant 1) and N1814 (mutant 2), these TRIM-containing proteins are also affected by certain alanine substitutions in the C-terminal part of the CBP TRAM. This is in contrast to E1A, which was not affected by these mutations. For example, the mutation K1821A (mutant 9) affects all three proteins (p53, TFIIB, and YY1), while Q1822A (mutant 10) affects p53, and YY1, but not TFIIB. In addition to this, YY1 is also affected by additional mutations that do not affect either p53 or TFIIB.

Together, these results provide a precedent that variants of the TRAM sequence (whether naturally occurring or created by mutagenesis) can show differential binding to different TRIM-containing proteins. Consequently, if multiple changes were introduced it might be possible to express TRAM-containing proteins or peptides that displayed selective specificity that upon binding to particular TRIM-proteins could inhibit their interaction with other TRAMs. One example where this might be desirable would be with "high risk" HPV E6 protein where binding of a synthetic TRAM-containing peptide to E6 might be used to prevent an E6-CBP interaction to inhibit the effect that E6 has on p53.

EXAMPLE 2

Materials and Methods

Plasmid constructs. The vector used for the expression of GST-fusion proteins, unless otherwise stated, was pGEX-2TKP (a modified version of the Pharmacia pGEX-2TK vector containing a polylinker, Bannister & Kouzarides 1995) which was a gift from Tony Kouzarides. Also a gift from T. Kouzarides were the plasmids GST-CBP I (residues 461–662), GST-CBP II (residues 1621–1877), GST-P/CAF, GST-E1A [1–90] (residues 1–90 of the adenovirus E1A protein), G5E1BCAT, pHK3NVP16, pHKnTCBPIVP16, pHKnCBPIIVP16 and pHKGT. This last construct contains the DNA binding domain of GAL4 (1–147) driven by an SV40 promoter and was used to create the GAL4-HPV-E6 fusion proteins GAL-11E6 and GAL-16E6. Plasmids GST-11E6 and GST-16E6 were created by inserting HPV-11 and HPV-16 E6 sequences amplified by PCR into pGEX2TKP. The GST-6E6 and GSTF-18E6 constructs used to express the full-length HPV-6 and 18 E6 proteins respectively, were a kind gift from David Pim (Pim et al, 1997). The GST-E6AP expression vector was kindly provided by Elliot Androphy (Huibregtse et al, 1991). The GST-CBP constructs described in FIG. 8 (1 to 8) were created by cloning PCR amplified fragments into pGEX2TKP. The MBP-CBP fusion construct was created by cloning a CBP fragment (residues 1808–1852) from pGEX2TKP into the vector pMALP, a modified version of pMAL (NEB) containing a polylinker (FIG. 13) that was a gift from Edward Manser. Also provided by Dr. Manser was the in vitro transcription and mammalian expression vector pXJ-FLAG (Manser et al, 1997). The original DNA for the HPV-16 E6 mutant L50G was a kind gift from Tadahito Kanda (Nakagawa et al, 1995) and was cloned via the BamH1 and Xho1 restriction sites into pXJ-FLAG. All the other constructs used for in vitro transcription reactions were cloned BamHI/HindIII into pXJ-FLAG.

Expression of recombinant bacterial fusion-proteins. GST-fusion and MBP-fusion proteins were expressed in *E. coli*, extracted with lysis buffer (50 mM Tris-HCl pH 8.0, 0.5 mM EDTA, 5 mM DTT, 15% glycerol, 1 mg/ml lysozyme and 1 mM PMSF), and after sonication and centrifugation, stored at −70° C.

Partial-purification of CBPlp300 from HeLa Nuclear extract. HeLa nuclear extract was diluted 1:3 with 20 mM MES buffer pH 6.1, 10 mM NaF, and 0.1% Triton X-100, before being passed over a 0.2 ml SP Sepharose ion-exchange column (Pharrnacia) equilibrated with the same buffer. Elution of CBP/p300 using a step gradient of increasing [KCl] was maximal in the 300 mM and 400 mM KCl fractions (as determined by Western blot analysis using an anti-p300 antibody, data not shown). These two fractions were pooled and then diluted 1:7 with binding buffer (20 mM Tris-HCl, pH 8.0, 0.5 mM EDTA, 0.5 mM DTT, 20% glycerol, 01% NP40) to bring the final salt concentration down to 50 mM KCl. The partially purified CBP/p300 was then passed over GST-fusion protein micro-affinity columns as described below.

Detection of protein-protein interactions using micro-affinity columns. Bacterial lysate containing GST-fusion protein was incubated with glutathione-Sepharose beads (Pharmacia) for 30 min at 4° C. in 1×NENT buffer (100 mM NaCl, 1 mM EDTA, 0.5% NP-40, Tris-HCl, pH 8.0). After spinning down and washing with 1 ml 1×NENT, the beads were loaded into a yellow Gilson pipette tip containing a glass bead (BDH, cat. no. 332134Y) to create a 25 1 GST micro-column. For MBP micro-columns, a similar approach was taken in which amylose resin (NEB) was used in place of glutathione-Sepharose beads. These columns were then used to detect interactions with in vitro translated and radiolabelled proteins, bacterially expressed fusion proteins, or partially purified nuclear CBP/p300.

For in vitro translation (IVT) proteins, expression and incorporation of $^{35}$S-methionine was performed using TNT kits (Promega) according to the manufacturer's recommendations. After a 1 hr incubation at 30° C., 40 $\mu$l of a 50 $\mu$l IVT reaction was diluted with 360 $\mu$l of IPD buffer (50 mM KCl, 40 mM Hepes, pH 7.5, 5 mM 2-Mercaptoethanol, 0.1% Tween-20, 0.5% milk) before being passed over the GST micro-column. After washing the column twice with 200 $\mu$l wash buffer (IPD buffer containing 150 mM KCl), proteins were eluted from the column by adding 25 $\mu$l of 2×SDS loading dye, heating to 95° C. for 5 min, chasing with 25 1 water, and spinning in a micro-centrifuge. Samples were then analysed by SDS PAGE and, after staining and drying down the gel, proteins were detected via exposure to autoradiographic film.

In order to detect the interaction between two bacterially expressed recombinant proteins, GST-fusion proteins were passed down MBP-fusion micro-affinity columns or vice versa. After purification of the target recombinant fusion protein on glutathione Sepharose beads or amylose resin, the proteins were eluted using recombinant binding buffer (RBB) (25 mM Hepes, pH 7.6, 50 mM KCl, 12.5 mM $MgCl_2$, 10% glycerol, and 0.1% NP40). In addition to the RBB, either 10 mM reduced glutathione (Sigma) (for GST-proteins) or 20 mM maltose (for MBP-fusion proteins) was present. After passing the recombinant target protein in RBB over the micro-affinity column and washing using RBB containing 150 mM KCl, the samples were eluted as described above for IVT proteins and run on SDS gels. Samples were then transferred onto polyvinylidene difluoride (PVDF) membranes and GST or MBP fusion proteins detected using the appropriate antibodies by Western blot analysis (see below). A similar analysis was performed for the partially purified nuclear CBP/p300 proteins. In this case the binding buffer consisted of 20 mM Tris-HCl, pH 8.0, 50 mM KCl, 0.5 mM EDTA, 0.5 mM DTT, 20% glycerol, 01% NP40, and CBP/p300 was detected by Western analysis using antibodies specific for these proteins.

Western blot analysis. Proteins analysed on 0.75 mm thick SDS-PAGE gels were blotted onto PVDF membranes (NEN) overnight. The membranes were blocked with 5% (w/v) nonfat dry milk in TBST (10 mM Tris-HCl, pH 8.0, 150 mM NaCl, 0.05% Tween 20). A 1 hr incubation at room temperature with the first monoclonal antibody was performed followed by washing with TSBT. The membrane was then incubated for 30 min with a horseradish peroxidase-coupled second antibody (1:4,000; DAKO) before washing in TSBT. Proteins were visualised with hyperfilm in the presence luminol (Amersham) for 10 to 60 s, depending on signal intensity.

Mammalian two hybrid-experiments. To study protein-protein interactions in vivo we made use of a Gal4-VP16 CAT reporter system described previously (Bannister & Kouzarides 1995). Full-length HPV 11 E6 and 16 E6 sequences were fused to the DNA binding domain of GAL4 resulting in the constructs pGAL4–11E6 and pGAL4–11E6, respectively. U2-OS cells were co-transfected with 1 μg pGAL4–11E6 or pGAL4–11E6 and 4 μg pG5E1BCAT (a CAT reporter vector containing multiple GAL4 DNA-binding sites). Co-transfected together with these plasmids was either pHK3NVP16 (the activation domain of VP16, residues 415–490 driven by the SV40 promoter), 2 μg pHKnTCBP1VP16 (expressing CBP residues 461–662 in frame with the VP 16 activation domain), or 2 μg pHKnCBP2VP16 (expressing CBP residues 1621–1877 in frame with the VP 16 activation domain). 48 hours after transfection the cells were harvested and CAT assays performed as described below.

In vitro p53 degradation assay. E6-mediated degradation of p53 was assayed using a previously described method (Nakagawa et al, 1995; Scheffer et al, 1993). Essentially, 12.5 μl of in vitro translated E6 protein was mixed with 2 1 of in vitro translated and $^{35}$S-labelled p53 in a total volume of 25 μl of assay buffer (25 mM Tris-HCl (pH7.5), 100 mM NaCl, 3 mM DTT). The sample was then incubated at RT for 30, 90, or 180 min. At the indicated time points the reaction was stopped by adding 2×SDS loading dye and boiling for 5 min. The samples were then analysed by SDS PAGE and autoradiography.

Transfections and CAT assays. U-2OS cells were plated onto 10-cm-diameter culture dishes and transfected at 50–70% confluency using lipofectin reagent (GIBCO-BRL). Chloramphenicol acetyl transferase (CAT) assays have been described elsewhere (O'Conner & Bernard, 1995) and the data presented represent between three and eight experiments using at least two independent DNA preparations.

Results

Figure 7A:
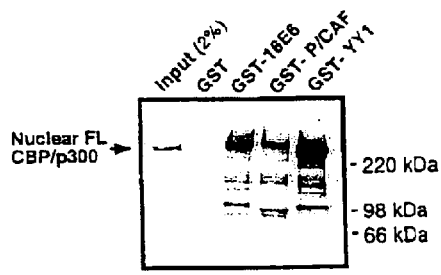

The HPV-16 E6 protein interacts with full-length nuclear CBP/p300. In order to determine whether or not the papillomavirus E6 protein could interact with CBP/p300, we partially purified these transcriptional coactivators from HeLa nuclear extract (see Materials and Methods) and then passed the fraction enriched for CBP/p300 over an E6 affinity column. Western analysis using the monoclonal antibodies p300 Ab-1 (FIG. 7A), and NM11 (data not shown), detected a specific interaction between CBP/p300 and GST-16E6. No interaction was detected for the control GST column, even though a greater amount of protein was used. Also shown in FIG. 7A is the interaction between full-length nuclear CBP/p300 and GST-P/CAF, and GST-YY1. These data provide the first evidence that a papillomavirus oncoprotein can associate with the transcriptional co-activator CBP/p300.

Figure 7B:
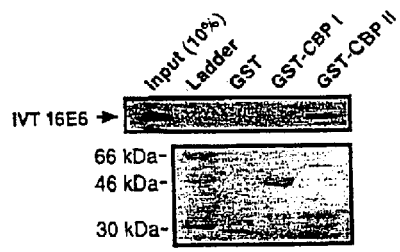
Figure 7C:
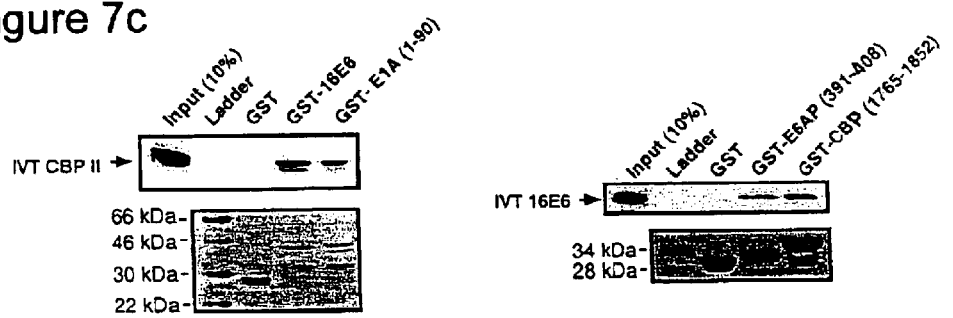

Both Ad E1A and SV40 TAg bind the CBP II domain of CBPI(residues 1621–1877) which represents a hot spot for transcription factor interactions. We tested whether or not HPV-16 E6 was also able to bind to this region of CBP using a micro-affinity column (described in Materials and Methods) containing GST-CBP (1621–1877). In FIG. 7B it cap be seen that in vitro translated and radiolabelled HPV-16 E6 does indeed bind to the GST-CBP II domain, but not to GST or to GST-CBP I (461–662), another region of CBP that binds multiple cellular transcription factors. Furthermore, our unpublished results suggest that unlike E1A, HPV-16 E6 does not bind to multiple regions of CBP/p300 but is limited to the CBP II domain.

In order to gain an insight into the relative strength of the E6-CBP II association, we compared this protein-protein interaction with two previously described interactions, namely that of E1A and the CBP II domain, and the binding of HPV E6 to the cellular factor E6AP. As can be seen from the results presented in FIG. 7C, the association of HPV-16 E6 with the CBP II domain is of a similar strength to those seen with the two previously documented interactions. Nevertheless, it should be noted that while HPV-16 E6 and Ad E1A bind the CBP II domain at a comparable level, E1A binds full-length nuclear CBP/p300 with a much higher affinity. This is most likely due to the fact that E1A can bind multiple sites on CBP/p300 in addition to the CBP II domain.

Figure 7D:
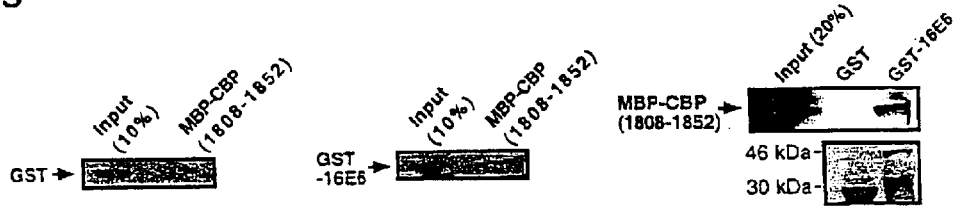

FIG. 7D demonstrates that the interaction between HPV-16 E6 and the CBP II domain can occur directly, since binding can be detected using only purified, recombinant proteins. The interaction of GST-16E6 with an MBP-CBP affinity column was detected by western analysis using specific GST antibodies, while in the reciprocal experiment MBP-CBP binding to a GST-E6 column was detected using an anti-MBP antibody.

Together, these results provide evidence that the human papillomavirus type-16 E6 protein can associate with full-length nuclear CBP/p300 via the CBP II domain in an interaction that is most likely direct. Interestingly, we have not been able to detect the interaction of HPV-16 E6 with full-length in vitro translated CBP or p300, suggesting that post-translational modification of CBP/p300 may be required for the interaction with HPV-16 E6.

Characterisation of the HPV-16 E6-CBP interaction. In order to determine the E6 binding site within the CBP II domain, we utilised a number of GST-CBP constructs in micro-affinity column assays with in vitro translated and radiolabeled full-length HPV-16 E6 protein (see FIG. 8). We were able to identify a 19 amino acid region of CBP (1808–1826) that was capable of binding full-length E6 (lane 7). Deletion into this sequence abolished binding to the E6 protein (lane 8).

Interestingly, these CBP residues, presented in FIG. 8, are identical to those we recently characterised as the binding site for the Ad E1A protein, as well as numerous cellular transcription factors including p53. Indeed, FIG. 8 also shows the ability of a wild type E1A peptide that can bind the 19 amino acid CBP sequence to inhibit the HPV-16 E6-CBP interaction. A mutant E1A peptide that is unable to bind CBP fails to inhibit the E6-CBP interaction. It can be seen that this sequence is virtually identical in both CBP and p300, with only one conservative change in the 19 amino acid segment. This sequence is also highly conserved in other CBP/p300, and may represent the major transcription factor-binding site within the CBP II domain species.

A similar analysis of the CBP-binding site-within HPV-16 E6 was also performed. As can be seen from FIG. 9, removal of the C-terminal residues 148–151 that have been implicated in the binding of another E6-interacting protein, hDLG, had no effect on CBP banding. Dissection of the HPV-16 E6 protein into N-terminal (1–84) and C-terminal (85–151) halves demonstrated that while the N-terminus of E6 does not bind CBP, the C-terminal half of the protein maintained the ability to bind CBP, as did a smaller C-terminal region (amino acids 100–147).

In the context of a GST-fusion protein (E6 amino acids 100–142), the cystein residues (C103, C139 and C140) could be substituted with glycine residues without affecting the ability to bind CBP (our unpublished results). This suggests that specific sequences within the second zinc finger of E6 are involved in the interaction with CBP and that, at least in this context, an intact zinc finger structure is not necessary. However, we have not tested these mutations in the context of full-length E6 alone, and cannot therefore rule out that an intact zinc finger structure is necessary to present the E6 residues contacting CBP under these conditions. We are currently attempting to define more precisely the HPV-16 E6 residues involved in the interaction with CBP.

"High-risk" but not "low-risk" HPV E6 proteins bind CBP/p300. It has been suggested that functional differences between the E6 and E7 proteins of different HPVs is a cardinal factor in the ability of these viruses to transform cells and is also reflected by their classification as either high-risk or low-risk. In the case of other DNA tumour virus proteins, such as the Ad E1A protein and the SV40 TAg, interaction with the transcriptional coactivators CBP/p300 has been shown to be absolutely required for their transforming capabilities. If CBP/p300 is considered an important target in the transformation processes of other DNA tumour viruses, we postulated that an ability to target CBP/p300 might also be an important factor in distinguishing high-risk E6 proteins from low-risk proteins. Consequently, we investigated the ability of another high-risk E6 protein (from HPV-18) to bind CBP, and compared this, along with HPV-16 E6, to two low-risk E6 proteins from HPV-6 and HPV-11.

FIG. 10A does in fact show that only the GST-E6 proteins of the high-risk types (HPV-16 and HPV-18) can bind to in vitro translated CBP II, while those of the low-risk types (HPV-6 and HPV-11) fail to bind CBP above the background level. This observation is reproducible, as can be seen from the inability of in vitro translated HPV-11 E6 protein to bind to a GST-CBP affinity column.

This difference in CBP binding is also observed in vivo, as demonstrated by the mammalian two-hybrid assay presented in FIG. 10B. Transient co-transfection experiments were performed using U2-OS cells in which a CAT reporter construct, driven by multiple GAL4 binding sites (G5E1BCAT), was introduced along with either an expression vector for full-length HPV-11 E6 fused to the DNA binding domain of GAL4 (GAL-11E6), or a similar construct containing HPV-16 sequences (GAL-16E6). Activation of transcription was then determined for those cells containing these two plasmids in conjunction with either the expression vector for the VP16 activation domain alone, VP16 fused to the CBP I domain, or VP16 fused to the CBP II domain. The level of CAT activity obtained with cells co-transfected with the VP16 activation domain was set at one and the CAT activity of cells receiving either CBP I-VP16, or CBP II-VP16 was then compared to this.

As can be seen from the results in FIG. 10B, cells containing GAL-16E6 could be activated by CBP II-VP 16, while those containing the GAL-11E6 expression vector could not. This effect was specific for the 16E6-CBP II interaction, since VP16 sequences fused to the CBP I domain failed to activate GAL-16E6. Taken together, these results strongly suggest that there are functional differences between high-risk and low-risk proteins with respect to their ability to bind CBP/p300 both in vitro and in vivo.

The down-regulation of p53 transcriptional activity by HPV-16 E6 correlates with CBP binding. One of the main functions proposed for high-risk HPV E6 proteins is the targeting of p53 in order to suppress apoptosis of the host cell. In the last few years, many lines of evidence have suggested that one way in which this might be achieved is by stimulating the degradation of p53 through the ubiquitination pathway. Evidence has been provided both in vitro and in vivo that this activity is dependent upon the interaction of E6 with a cellular factor termed E6AP which then acts as a ubiquitin ligase. The ability of E6 proteins to interact with E6AP has been shown to be limited to those of high-risk HPV types. It has also been reported previously that high-risk but not low-risk E6 proteins are able to down-regulate p53 transcriptional activity. One explanation for these observations is that down-regulation of p53-dependent transcription results from the E6AP-dependent degradation of p53.

Recently, it was also shown that p53-dependent transcription can be activated by CBP/p300 and that this activation can be abrogated by wild type E1A, but not a CBP-binding deficient mutant of E1A. The results presented here have demonstrated that like E1A, high-risk HPV E6 proteins can also target CBP/p300. We therefore asked the question whether or not the down-regulation of p53 transcriptional activity by high-risk E6 proteins could be achieved through the binding of CBP/p300 in a similar fashion to E1A.

In order to answer this question, we required a high-risk E6 mutant that was deficient in targeting p53 for degradation through the E6AP pathway yet was still capable of binding CBP/p300. We analysed a number of existing HPV-16 E6 mutants before finding one with the desired properties. The 16E6 mutant L50G contains a point mutation in the first zinc finger of the E6 protein and has previously been shown to be p53-degradation-deficient. FIG. 11A demonstrates that this mutant is still able to interact with CBP in binding assays. However, when we tested this mutant for its ability to bind E6AP in a similar assay, we found that it was deficient in this capacity (see FIG. 11B). Furthermore, FIG. 11C confirms that this mutant, like the low-risk HPV-11 E6 protein, is unable to degrade p53 using a standard degradation assay previously described.

We next carried out a series of experiments in which we assessed the ability of the 16E6 L50G mutant to down-regulate p53-dependent transcription. U2-OS cells were transfected with the p53-responsive CAT reporter PG13CAT or the control vector MG15CAT. Co-transfected with PG13CAT were various expression plasmids coding for E6 proteins or 12S E1A. It can be seen from FIG. 12A that the PG13CAT is stimulated by endogenous p53 in U2-OS cells in a manner dependent upon intact p53-binding sites. The level of transcriptional activity obtained with PG13CAT is not affected by the introduction of an expression vector containing full-length HPV-11 E6 sequences. By contrast, the expression of wild type 16E6 protein results in a significant reduction in p53-dependent transcription. Consistent with our earlier analysis of the CBP-binding domain within 16E6, the N-terminal 84 amino acids that do not bind CBP, fail to repress p53 activity, while the C-terminal half of 16E6 that contains the CBP-binding domain can repress p53-dependent transcription, albeit slightly less efficiently than the full-length protein. Also shown for comparison is the level of repression of p53 activity obtained upon the introduction of the adenovirus 12S E1A protein. Significantly, the 16E6 L50G mutant results in a similar level of transcriptional repression as the wild type HPV-16 E6 protein. Thus, in this respect the 16E6 L50G mutant does not behave like a low-risk protein, but rather like wild type 16E6. These data provide evidence that are consistent with the idea that by targeting CBP/p300 a high-risk E6 protein can repress p53 transcriptional activity. Furthermore, the use of the 16E6 L50G mutant suggests this ability is independent of E6AP-mediated degradation.

We wished to provide further evidence that the repression of p53 transcriptional activity by 16E6, 16E6 L50G, and E1A was due to the targeting of CBP/p300. Therefore, we over-expressed full-length CBP in a similar set of transfection experiments and asked whether or not the observed superactivation of p53-dependent transcription could be abrogated by these proteins. FIG. 12B demonstrates that the co-transfection of full-length CBP into U2-OS cells stimulates p53-dependent transcription by approximately 7-fold. Like E1A, both wild type 16E6 and the 16E6 L50G mutant abolish this CBP-induced superactivation of p53-dependent transcription. This is in contrast to HPV-11 E6 which is severely abrogated in this capacity.

In summary, the results presented in FIGS. 11 and 12 provide evidence that high-risk E6 proteins possess an additional and, up until now, undiscovered mechanism by which to down-regulate p53 activity. That is, by targeting CBP/p300 high-risk E6 proteins can abrogate p53-dependent transcription in a fashion analogous to adenovirus E1A.

References

Bannister, A. J. and T. Kouzarides., 1996, CPB-induced stimulation of c-Fos activity is abrogated by E1A. EMBO. J. 14: 4758–4762.

Huibregtse, J. M., M. Scheffner, and P. M. Howley, 1991, A cellular protein mediates association of p53 with the E6 oncoprotein of human papillomavirus types 16 or 18. EMBO J. 10:4129–4135.

Manser, E., H. Y. Huang, T. H. Loo, X. Q. Chen, J. M. Dong, T. Leung, and L. Lim., 1997, Expression of constitutively active alpha-PAK reveals effects of the kinase on actin and focal complexes. Mol. Cell. Biol. 17:1129–1143.

Nakagawa, S., S. Watanabe, H. Yoshikawa, Y. Taketani, K. Yoshiike, and T. Kanda, 1995, Mutational analysis of human papillomavirus type 16 E6 protein; transforming function for human cells and degradation of p53 in vitro., Virology 212, 535–542.

O'Conner, M. and H. U. Bernard, 1995, Oct-1 activates the epithelial-specific enhancer of human papillomarvirus type 16 via a synergistic interaction with NFI at a conserved composite regulatory element., Virology 207, 77–88.

O'C.onnor, M. J., S. H. Tan, C. H. Tan, and H. U. Bernard. 1996. YY1 represses human papillomavirus type 16 transcription by quenching AP-1 activity. J. Virol. 70: 6529–6539.

Pim, D., P. Massimi, and L. Banks, 1997, Alternatively spliced HPV-18 E6* protein inhibits E6 mediated degradation of p53 and suppresses transformed cell growth. Oncogene 15, 257–264.

Scheffner, M., J. M. Huibregtse, R. D. Viersta, and P. M. Howley, 1993, The HPV-16 E6 and E6-AP complex functions as a ubiquitin-protein ligase in the ubiquitination of p53. Cell 75, 496–505.

Smith, D. B., and Johnson, K. S. 1988. Single-step purification of polypeptides expressed in Escherichia coli as fusions with glutathione S-transferase. Gene 67: 31–40.

Xiao, J. H., I. Davidson, H. Matthes, J. -M. Gamier, and P. Chambon. 1991. Cloning, expression and transcriptional properties of the human enhancer factor TEF-1. Cell 65: 551–568.

Unckell, F., Streeck, R., and Sapp, M. 1997. J. Virol. 71(4): 2934–2939.

What is claimed is:

1. A method for determining whether a compound is capable of inhibiting an interaction between a first polypeptide and a second polypeptide said method comprising:
   (a) (i) incubating said first polypeptide with said second polypeptide in vitro under conditions which allow the first polypeptide to bind to the second polypeptide to form a complex; and bringing the complex thus formed into contact with a candidate compound; or
   (ii) incubating said first polypeptide with said second polypeptide in vitro in the presence of a candidate compound under conditions which would allow the first polypeptide to bind to the second polypeptide in the absence of the candidate compound; and
   (b) determining if said candidate compound inhibits binding of the first polypeptide to the second polypeptide;
   wherein said first polypeptide comprises a Transcriptional Adaptor Motif (TRAM) sequence of any one of the sequences shown in SEQ ID NO: 3 to 9 and said second polypeptide is a human papillomavirus (HPV) polypeptide E6 of HPV-16 or HPV-18 comprising a sequence which binds to a said TRAM sequence.

2. The method according to claim 1 wherein said first polypeptide is a polypeptide found in eukaryotic cells.

3. The method according to claim 2 wherein said eukaryotic polypeptide is selected from transcription factors and cell cycle regulatory proteins.

4. The method according to claim 2 wherein said eukaryotic polypeptide is selected from mdm2 comprising a sequence of SEQ ID NO:6 or 7, CREB binding protein (CBP) comprising a sequence of SEQ ID NO:3, 4 or 5, and p300 comprising a sequence of SEQ ID NO: 8 or 9.

5. The method according to claim 1 wherein the first polypeptide is CREB binding protein (CBP) comprising a sequence of SEQ ID NO:3, 4 or 5.

6. The method according to claim 1 wherein the sequence which binds said TRAM sequence is located within the second zinc finger of HPV-16 or -18 E6 protein.

7. The method according to claim 1 wherein said first polypeptide is p300 comprising a sequence of SEQ ID NO:8 or 9.

8. The method according to claim 1 wherein said second polypeptide comprises the sequence of amino acids 100 to 147 of SEQ ID NO: 18.

9. The method according to claim 1 wherein the first polypeptide is mdm2 comprising a sequence of SEQ ID NO:6 or SEQ ID NO:7.

* * * * *

SEQUENCE LISTING

```
<160> NUMBER OF SEQ ID NOS: 36

<210> SEQ ID NO 1
<211> LENGTH: 12
<212> TYPE: PRT
<213> ORGANISM: Artificial Sequence
<220> FEATURE:
<221> NAME/KEY: VARIANT
<222> LOCATION: (1)
<223> OTHER INFORMATION: Xaa represents Lys or Arg
<220> FEATURE:
<221> NAME/KEY: VARIANT
<222> LOCATION: (2)
<223> OTHER INFORMATION: Xaa represents Lys or Arg
<220> FEATURE:
<221> NAME/KEY: VARIANT
<222> LOCATION: (3)
<223> OTHER INFORMATION: Xaa represents any amino acid
<220> FEATURE:
<221> NAME/KEY: VARIANT
<222> LOCATION: (5)
<223> OTHER INFORMATION: Xaa represents any amino acid
<220> FEATURE:
<221> NAME/KEY: VARIANT
<222> LOCATION: (6)
<223> OTHER INFORMATION: Xaa represents any amino acid
```

```
<220> FEATURE:
<221> NAME/KEY: VARIANT
<222> LOCATION: (9)
<223> OTHER INFORMATION: Xaa is Val or Ile
<220> FEATURE:
<221> NAME/KEY: VARIANT
<222> LOCATION: (11)
<223> OTHER INFORMATION: Xaa represents Lys or Arg
<220> FEATURE:
<221> NAME/KEY: VARIANT
<222> LOCATION: (12)
<223> OTHER INFORMATION: Xaa represents any amino acid
<220> FEATURE:
<223> OTHER INFORMATION: Description of Artificial Sequence: consensus
      sequence of transcriptional adaptor motif (TRAM)

<400> SEQUENCE: 1

Xaa Xaa Xaa Asn Xaa Xaa Cys Pro Xaa Cys Xaa Xaa
 1               5                  10

<210> SEQ ID NO 2
<211> LENGTH: 13
<212> TYPE: PRT
<213> ORGANISM: Artificial Sequence
<220> FEATURE:
<221> NAME/KEY: VARIANT
<222> LOCATION: (1)
<223> OTHER INFORMATION: Xaa represents Lys or Arg
<220> FEATURE:
<221> NAME/KEY: VARIANT
<222> LOCATION: (2)
<223> OTHER INFORMATION: Xaa represents Lys or Arg
<220> FEATURE:
<221> NAME/KEY: VARIANT
<222> LOCATION: (3)
<223> OTHER INFORMATION: Xaa represents any amino acid
<220> FEATURE:
<221> NAME/KEY: VARIANT
<222> LOCATION: (5)
<223> OTHER INFORMATION: Xaa represents any amino acid
<220> FEATURE:
<221> NAME/KEY: VARIANT
<222> LOCATION: (6)
<223> OTHER INFORMATION: Xaa represents any amino acid
<220> FEATURE:
<221> NAME/KEY: VARIANT
<222> LOCATION: (9)
<223> OTHER INFORMATION: Xaa represents Val or Ile
<220> FEATURE:
<221> NAME/KEY: VARIANT
<222> LOCATION: (11)
<223> OTHER INFORMATION: where Xaa represents Lys or Arg
<220> FEATURE:
<221> NAME/KEY: VARIANT
<222> LOCATION: (12)
<223> OTHER INFORMATION: Xaa represents any amino acid
<220> FEATURE:
<223> OTHER INFORMATION: Description of Artificial Sequence: consensus
      sequence of transcriptional adaptor motif (TRAM)

<400> SEQUENCE: 2

Xaa Xaa Xaa Asn Xaa Xaa Cys Pro Xaa Cys Xaa Xaa Ile
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:derived from
      CBP

<400> SEQUENCE: 3

Arg Lys Thr Asn Gly Gly Cys Pro Val Cys Lys Gln
```

```
<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence:derived from
      CBP

<400> SEQUENCE: 4

Arg Lys Thr Asn Gly Gly Cys Pro Val Cys Lys Gln Pro Ile
 1               5                  10

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence:derived from
      CBP

<400> SEQUENCE: 5

Gly Cys Lys Arg Lys Thr Asn Gly Gly Cys Pro Val Cys Lys Gln Leu
 1               5                  10                  15
Ile Ala Leu

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:derived from
      Mdm-2

<400> SEQUENCE: 6

Lys Lys Arg Asn Lys Pro Cys Pro Val Cys Arg Gln
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence:derived from
      Mdm-2

<400> SEQUENCE: 7

Lys Lys Arg Asn Lys Pro Cys Pro Val Cys Arg Gln Pro Ile
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:derived from
      p300

<400> SEQUENCE: 8

Arg Lys Thr Asn Gly Gly Cys Pro Ile Cys Lys Gln
 1               5                  10

<210> SEQ ID NO 9
<211> LENGTH: 14
<212> TYPE: PRT
<213> ORGANISM: Artificial Sequence
<220> FEATURE:
```

```
<223> OTHER INFORMATION: Description of Artificial Sequence:derived from
      p300

<400> SEQUENCE: 9

Arg Lys Thr Asn Gly Gly Cys Pro Ile Cys Lys Gln Leu Ile
  1               5                  10

<210> SEQ ID NO 10
<211> LENGTH: 7
<212> TYPE: PRT
<213> ORGANISM: Artificial Sequence
<220> FEATURE:
<221> NAME/KEY: VARIANT
<222> LOCATION: (2)
<223> OTHER INFORMATION: Xaa represents any amino acid
<220> FEATURE:
<221> NAME/KEY: VARIANT
<222> LOCATION: (3)
<223> OTHER INFORMATION: Xaa represents Glu or Asp
<220> FEATURE:
<221> NAME/KEY: VARIANT
<222> LOCATION: (4)..(6)
<223> OTHER INFORMATION: Xaa represents any amino acid
<220> FEATURE:
<223> OTHER INFORMATION: Description of Artificial Sequence: consensus
      sequence of Transcriptional interaction motif(TRIM)

<400> SEQUENCE: 10

Phe Xaa Xaa Xaa Xaa Xaa Leu
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: derived
      from E1A

<400> SEQUENCE: 11

Phe Pro Glu Ser Leu Ile Leu
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:derived from
      p53

<400> SEQUENCE: 12

Phe Ser Asp Leu Trp Lys Leu
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:derived from
      TFIIB

<400> SEQUENCE: 13

Phe Lys Glu Ile Thr Thr Met
  1               5

<210> SEQ ID NO 14
<211> LENGTH: 7
```

```
<212> TYPE: PRT
<213> ORGANISM: Artificial Sequence
<220> FEATURE:
<223> OTHER INFORMATION: Description of Artificial Sequence:derived from
      YY1

<400> SEQUENCE: 14

Phe Glu Asp Gln Ile Leu Ile
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:derived from
      YY1

<400> SEQUENCE: 15

Phe Arg Asp Asn Ser Ala Met
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:derived from
      YY1

<400> SEQUENCE: 16

Phe Val Glu Ser Ser Lys Leu
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:derived from
      MyoD

<400> SEQUENCE: 17

Phe Tyr Asp Asp Pro Cys Phe
 1               5

<210> SEQ ID NO 18
<211> LENGTH: 151
<212> TYPE: PRT
<213> ORGANISM: Human papillomavirus

<400> SEQUENCE: 18

Met Phe Gln Asp Pro Gln Glu Arg Pro Arg Lys Leu Pro Gln Leu Cys
 1               5                  10                  15

Thr Glu Leu Gln Thr Thr Ile His Asp Ile Ile Leu Glu Cys Val Tyr
                20                  25                  30

Cys Lys Gln Gln Leu Leu Arg Arg Glu Val Tyr Asp Phe Ala Phe Arg
            35                  40                  45

Asp Leu Cys Ile Val Tyr Arg Asp Gly Asn Pro Tyr Ala Val Cys Asp
        50                  55                  60

Lys Cys Leu Lys Phe Tyr Ser Lys Tyr Ser Glu Tyr Arg His Tyr Cys
 65                  70                  75                  80

Tyr Ser Leu Tyr Gly Thr Thr Leu Glu Gln Gln Tyr Asn Lys Pro Leu
                85                  90                  95
```

```
Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence:derived from
      E1A

<400> SEQUENCE: 19

Val Asn Glu Phe Phe Pro Glu Ser Leu Ile Leu Ala Ala
  1               5                  10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence:derived from
      E1A

<400> SEQUENCE: 20

Val Asn Glu Phe Phe Pro Ala Ser Ala Ile Leu
  1               5                  10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:derived from
      E1A

<400> SEQUENCE: 21

Val Asn Glu Phe Ala Pro Ala Ser Ala Ile Ala
  1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence:derived from
      p53

<400> SEQUENCE: 22

Ser Gln Glu Thr Phe Ser Asp Leu Trp Lys Leu Leu Pro
  1               5                  10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence:derived from
      E2F

<400> SEQUENCE: 23
```

```
Phe Asp Cys Asp Phe Gly Asp Leu Thr Pro Leu Asp Phe
  1               5                  10
```

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence:derived from
      Mdm-2

<400> SEQUENCE: 24

```
Lys Lys Leu Lys Lys Arg Asn Lys Pro Cys Pro Val Cys Arg Gln Pro
  1               5                  10                  15

Ile Gln Met
```

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence:derived from
      CBP

<400> SEQUENCE: 25

```
Gly Cys Lys Arg Lys Thr Asn Gly Gly Cys Pro Val Cys Lys Gln Leu
  1               5                  10                  15

Ile Ala Leu
```

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence:derived from
      E1A

<400> SEQUENCE: 26

```
Val Asn Glu Phe Phe Pro Glu Ser Leu Ile Leu Ala Ala
  1               5                  10
```

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence:derived from
      p53

<400> SEQUENCE: 27

```
Ser Gln Glu Thr Phe Ser Asp Leu Trp Lys Leu Leu Pro
  1               5                  10
```

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence:derived from
      E2F

<400> SEQUENCE: 28

```
Phe Asp Cys Asp Phe Gly Asp Leu Thr Pro Leu Asp Phe
  1               5                  10
```

<210> SEQ ID NO 29

```
<211> LENGTH: 13
<212> TYPE: PRT
<213> ORGANISM: Artificial Sequence
<220> FEATURE:
<223> OTHER INFORMATION: Description of Artificial Sequence:derived from
      TFIIB

<400> SEQUENCE: 29

Met Met Asn Ala Phe Lys Glu Ile Thr Thr Met Ala Asp
 1               5                  10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence:derived from
      YY1

<400> SEQUENCE: 30

Ala Glu Asp Gly Phe Glu Asp Gln Ile Leu Ile Pro Val
 1               5                  10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence:derived from
      YY1

<400> SEQUENCE: 31

Cys Thr Lys Met Phe Arg Asp Asn Ser Ala Met Arg Lys
 1               5                  10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence:derived from
      YY1

<400> SEQUENCE: 32

Cys Gly Lys Ala Phe Val Glu Ser Ser Lys Leu Lys Arg
 1               5                  10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence:derived from
      MyoD

<400> SEQUENCE: 33

Thr Thr Asp Asp Phe Tyr Asp Asp Pro Cys Phe Asp Ser
 1               5                  10

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence:derived from
      CBP

<400> SEQUENCE: 34
```

```
Gly Cys Lys Arg Lys Thr Asn Gly Gly Cys Pro Val Cys Lys Gln Leu
 1               5                  10                  15

Ile Ala Leu

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence:derived
      from p300

<400> SEQUENCE: 35

Gly Cys Lys Arg Lys Thr Asn Gly Gly Cys Pro Ile Cys Lys Gln Leu
 1               5                  10                  15

Ile Ala Leu

<210> SEQ ID NO 36
<211> LENGTH: 49
<212> TYPE: DNA
<213> ORGANISM: Artificial Sequence
<220> FEATURE:
<223> OTHER INFORMATION: Description of Artificial Sequence: polylinker
      of plasmid pMALP

<400> SEQUENCE: 36
ggatccgtcg acctcgagcc cgggctgcag aagcttgatt gattagctt           49
```